United States Patent [19]

Ichijima et al.

[11] Patent Number: 4,764,454

[45] Date of Patent: Aug. 16, 1988

[54] COLOR PHOTOGRAPHIC MATERIAL WITH COLOR FORMING LIGAND COMPOUNDS AND A METHOD OF PROCESSING

[75] Inventors: Seiji Ichijima; Kei Sakanoue, both of Kanagawa, Japan

[73] Assignee: Fuji Photo Film Co., Ltd., Kanagawa, Japan

[21] Appl. No.: 943,127

[22] Filed: Dec. 18, 1986

[30] Foreign Application Priority Data

Dec. 20, 1985 [JP] Japan ................... 60-287064

[51] Int. Cl.$^4$ ............... G03C 7/26; G03C 7/32; G03C 7/18; G03C 7/40
[52] U.S. Cl. .................... 430/361; 430/223; 430/226; 430/359; 430/367; 430/378; 430/375; 430/542; 430/543; 430/547; 430/548; 430/549; 430/553; 430/555; 430/557; 430/558
[58] Field of Search ............ 430/359, 361, 367, 371, 430/375, 378, 542, 543, 547, 549, 222, 223, 226, 548, 553, 555, 557, 558 R

[56] References Cited

U.S. PATENT DOCUMENTS

| | | | |
|---|---|---|---|
| 2,533,182 | 12/1950 | Sargent | 430/375 |
| 4,555,477 | 11/1985 | Washburn | 430/359 |
| 4,555,478 | 11/1985 | Reczek et al. | 430/367 |
| 4,557,998 | 12/1985 | Washburn et al. | 430/359 |

*Primary Examiner*—Richard L. Schilling
*Attorney, Agent, or Firm*—Birch, Stewart, Kolasch & Birch

[57] ABSTRACT

A novel silver halide color photographic material is provided comprising a compound of the general formula (I):

$$\text{LIG-A-LVG} \qquad (I)$$

wherein A represents a group which reacts with an oxidation product of a developing agent to cleave the bond to LVG; LVG represents a coupling-off group; and LIG represents a group which reacts with metal ions to form a complex compound.

A novel method of processing the instant silver halide color photographic material is provided including a processing step using a processing solution of an iron (II) ion concentration of $1 \times 10^{-6}$ to 1 mol/l. In the processing step, the potential of a bath having a bleaching capacity containing an aminopolycarboxylic acid-iron (III) complex salt is 150 mV or less.

19 Claims, No Drawings

COLOR PHOTOGRAPHIC MATERIAL WITH COLOR FORMING LIGAND COMPOUNDS AND A METHOD OF PROCESSING

FIELD OF THE INVENTION

The present invention relates to a color photographic material comprising a novel compound capable of forming a complex compound and a method of processing said color photographic material. More particularly, the present invention relates to a color photographic material comprising a masking compound which allows color corrections without substantially causing a reduction in the photographic sensitivity. The present invention also relates to an image forming compound which allows for the formation of a color image which is excellent in image fastness. In addition, the present invention relates to a method of processing said color photographic material.

BACKGROUND OF THE INVENTION

One known approach to improve the color reproduction of a color photographic light-sensitive material includes a method which uses a colored coupler. The basic concept of such an approach is described in *PSA Journal*, Vol. 13 (page 94, 1947). This approach contemplates allowing a colored coupler to mask the deterioration in the color reproduction which is due to the unnecessary side absorption of light by a color forming dye of a coupler which is used in a color film.

However, this approach is disadvantageous because the incorporation of a colored compound in a light-sensitive layer involves a reduction in sensitivity. For example, in order to correct the side absorption of green light by a color forming dye of a cyan coupler, a magenta colored cyan coupler is generally added to the red-sensitive layer itself. It has been found that the absorption of light in the longer wavelength region by this magenta colored cyan coupler causes a shortage of light absorption in the shorter wavelength region of light by the red-sensitive layer. In particular, if a phenol cyan coupler as described in U.S. Pat. Nos. 4,333,999 and 4,451,559 is used as a cyan coupler, such a color forming dye shows much side absorption of light in the longer wavelength region. Therefore, a magenta colored cyan coupler is needed. However, the use of such a colored cyan coupler causes a remarkable reduction in the sensitivity of a red-sensitive layer.

It has also been found that the use of a yellow colored magenta coupler in a green-sensitive layer causes a shortage of light absorption which is necessary in the shorter wavelength region by the green-sensitive layer and hence a reduction in the sensitivity thereof for the same reason as described above.

On the other hand, U.S. Pat. No. 3,672,898 proposes a distribution of spectral sensitivity of blue-sensitive, green-sensitive and red-sensitive layers for more faithful color reproductivity. This approach contemplates shifting the spectral sensitivity of a red-sensitive layer to a shorter wavelength region which overlaps a large part of the spectral sensitivity distribution of a green-sensitive layer. Therefore, if a magenta colored cyan coupler is used in a red-sensitive layer, the absorption by the coupler causes a great shortage of light necessary for the red-sensitive layer which results in problems during the practical use of such a light-sensitive material for photography.)

Several approaches have been proposed to solve the above mentioned problems. For example, representative approaches for solving these problems are described in U.S. Pat. Nos. 4,427,763 and 4,555,477. However, it has been found that none of these approaches can be put into practical use because these approaches have a defect in molecular design. That is, in the former patent, precursors of yellow colored magenta couplers are disclosed. However, it is required that these couplers undergo coupling after being hydrolyzed. Therefore, this approach is poor in the speed of color formation. In the latter patent, couplers which allow a ligand for the formation of a complex compound to be separated from the coupling position thereof are disclosed. However, since these couplers need to contain a ligand in the coupling-off group, the range of coupling-off groups which can be selected is limited. As a result, the degree of freedom in selecting the coupling activity becomes small. In particular, if such a compound is used in a highly sensitive photographic light-sensitive negative which requires a highly reactive coupler it leaves much to be desired.

Many studies have been made heretofore to improve the image fastness of a color photographic light-sensitive material. One approach thus developed is to use a metal chelate. For example, U.S. Pat. No. 4,555,478 discloses a compound which cleaves a chelating agent from the coupling position of a coupler. However, it has been found that the compounds described in the above mentioned patent have a low coupling activity and thus are not suitable for use in the current highly sensitive light-sensitive materials.

SUMMARY OF THE INVENTION

Accordingly, an object of the present invention is to provide a highly sensitive color light-sensitive material which is excellent in color reproductivity and which comprises a color correcting masking compound having a high reactivity with an oxidation product of a developing agent and which causes a small reduction in sensitivity.

Another object of the present invention is to provide a color light-sensitive material which is excellent in image fastness and which comprises an image forming compound having a high reactivity with an oxidation product of a developing agent and is capable of forming a color image which is excellent in fastness.

These and other objects of the present invention will become more apparent from the following detailed description and examples.

The objects of the present invention are accomplished by using a silver halide color photographic material comprising a support having provided thereon at least one layer containing a compound represented by the general formula (I):

$$\text{LIG-A-LVG} \qquad \text{(I)}$$

wherein A represents a group which reacts with an oxidation product of a developing agent to cleave the bond to LVG; LVG represents a coupling-off group; and LIG represents a group which reacts with metal ions to form a complex compound.

DETAILED DESCRIPTION OF THE INVENTION

The compound of the general formula (I) will be further described hereinbelow.

In the general formula (I), A represents a coupling group or an oxidation reduction group. The term "coupling group" as used herein means a group which undergoes a coupling reaction with an oxidation product of a developing agent. Coupling groups which may be used include compounds analogous to couplers which have been heretofore known. The term "oxidation reduction group" as used herein means a group which is cross-oxidized by an oxidation product of a developing agent. Oxidation reduction groups which may be used include compounds analogous to oxidation reduction groups which have been heretofore known. When A represents a coupling group, LVG represents a group which is connected to the coupling position thereof and undergoes cleavage of its bond to A upon a coupling reaction. When A represents an oxidation reduction group, an oxidation product of a developing agent which has been produced by cross-oxidation undergoes a nucleophilic addition by a nucleophilic agent such as a hydroxyl ion and a sulfite ion present during development. LVG is connected to the carbon atom which undergoes such a nucleophilic addition. An elimination reaction following the nucleophilic addition involves A-LVG bond cleavage. Since the LVG group may be optionally selected from known coupling-off groups, the reaction rate may be easily controlled. In the general formula (I), LIG represents a ligand which may interact or coordinate with metal ions to form a metal chelate. Any known ligand may be used. LIG is connected to A at any position other than the position(s) at which it interacts or coordinates with the metal ions.

The compound of the general formula (I) is preferably diffusion resistant. More preferably, a diffusion resistant group is contained within the LVG group. Such a diffusion resistant group is a group for preventing the compound of the general formula (I) from moving or being diffused into other layers from the layer in which it has originally been incorporated with the compound. In general, an organic substituent for increasing the molecular weight of the compound is used. The LVG group may be a group containing one or more LIG-A-groups (bis type or polymer type).

If the compound produced by the reaction of the compound of the general formula (I) with an oxidation product of a developing agent is LIG-A' then LIG-A' preferably effuses or moves from the light-sensitive material so that it does not substantially remain therein.

The compound of the general formula (I) is preferably substantially colorless. The compound forms a metal chelate dye which substantially exhibits light absorption in the visible portion of the spectrum only when it forms a coordinate bond with metal ions upon development.

The reaction of the compound of the general formula (I) with an oxidation product of a developing agent which has been produced at the exposed portions of the photographic layer which incorporates the compound or at an adjacent light-sensitive layer in response to exposure involves an A-LVG bond cleavage. LIG-A' thus produced is preferably diffusable and therefore effuses from the light-sensitive material. The remaining LIG-A-LVG forms a complex compound in the layer which incorporates it after a processing step using metal ions so that it colors. Preferred examples of a dye thus produced include a cyan dye, a magenta dye and a yellow dye. In the above process, such a dye is formed in contrast with the image by which the light-sensitive material is exposed to light. This image may be used as a masking or a color image. In this case, this image may be combined with a negative silver halide emulsion to obtain a positive image.

Therefore, an example of the compound of the general formula (I) which is preferably used in the present invention is a compound of the general formula (II):

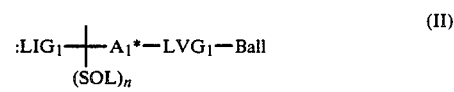

wherein $LIG_1$ represents a group which reacts with metal ions at the ":" side to form a complex compound so that it colors; $A_1^*$ represents a coupling group or an oxidation reduction group (when $A_1^*$ is a coupling group, * represents a coupling position whereas when $A_1^*$ represents an oxidation reduction group, the positions at which $A_1^*$ undergoes a nucleophilic addition by a nucleophilic species present during development upon cross-oxidation is represented by *); $LVG_1$ represents a coupling-off group which is linked to * of $A_1$; Ball represents an organic group for making the molecule of the compound large enough to be rendered diffusion resistant; SOL represents a dissociating group or quaternary ammonium salt for rendering the molecule of the compound water-soluble after $A_1^*$—$LVG_1$ bond cleavage so that it effuses from the light-sensitive material (SOL links to any position of: $LIG_1$—$A_1^*$—); and n represents an integer of 0 to 3, with the proviso that Ball may contain

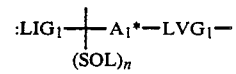

group wherein the compound of the general formula (II) is a bis compound or a polymer compound.

In the general formula (II), examples of the coupling group represented by $A_1^*$ include yellow coupler residual groups such as an open chain ketomethylene type coupler residual group, magenta coupler residual groups such as 5-pyrazolone type, pyrazoloimidazole type and pyrazolotriazole type coupler residual groups, cyan coupler residual groups such as phenol type and naphthol type coupler residual groups, and colorless coupler residual groups such as indanone type and acetophenone type coupler residual groups. Preferred examples of such coupling groups are shown hereinafter.

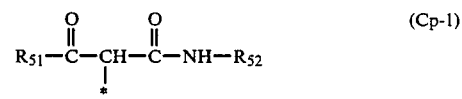
(Cp-1)

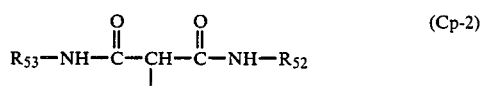
(Cp-2)

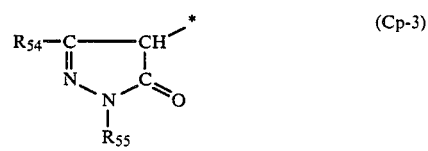
(Cp-3)

-continued

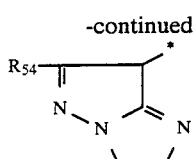
(Cp-4)

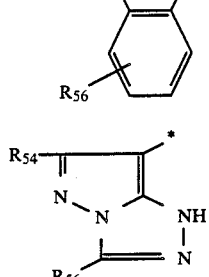
(Cp-5)

(Cp-6)

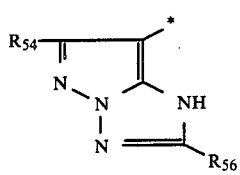
(Cp-7)

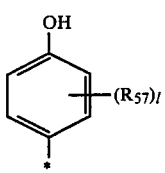
(Cp-8)

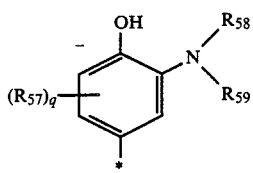
(Cp-9)

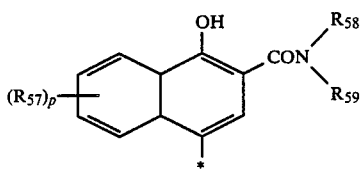
(Cp-10)

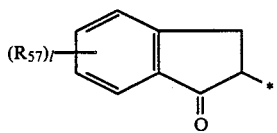

In the above general formulae, the free bond —* which comes from the coupling position represents the position at which the coupling-off group (—LVG$_1$—Ball) is connected thereto. In the above general formulae, R$_{51}$, R$_{52}$, R$_{53}$, R$_{54}$, R$_{55}$, R$_{56}$ and R$_{57}$ each represents a hydrogen atom or another substituent. The above coupling groups are connected to :LIG— and SOL at these positions directly or through these substituents as divalent groups. If the coupling group does not contain a group represented by :LIG or SOL, then R$_{51}$, R$_{52}$, R$_{53}$, R$_{54}$, R$_{55}$, R$_{56}$ and R$_{57}$ are properly selected from known substituents for the purpose of controlling the rate of coupling. However, the number of carbon atoms contained in such substituent is preferably 20 or less.

In the above general formulae, q represents an integer of 1 to 3, p represents an integer of 1 to 5, and l represents an integer of 1 to 4.

In the general formula (II), when A$_1$* represents an oxidation reduction group, it is specifically represented by the general formula (R-1):

$$B_1-P-(X=Y)_m-Q-B_2 \qquad (R-1)$$

wherein P and Q each represents an oxygen atom or a substituted or unsubstituted imino group, P and Q being different from each other; m represents an integer of 1 to 3 (at least one of X and Y represents a methine group containing —LVG$_1$—Ball as a substituent and at least one of the remaining X and Y represents a methine group containing :LIG— as a substituent; when SOL is contained in the molecule of the compound, e.g., when n is not 0 in the general formula (II), SOL may be contained in the substituent containing LIG— or at least one of the remaining X and Y represents a methine group containing SOL); and B$_1$ and B$_2$ each represents a group which can be removed by a hydrogen atom or alkali. Any two substituents of P, X, Y, Q, B$_1$ and B$_2$ may be connected to each other as divalent groups to form a cyclic structure. For example, (X=Y)$_m$ may form a benzene ring or pyridine ring.

When P and Q each represents a substituted or unsubstituted imino group, they are each preferably an imino group substituted by a sulfonyl group or an acyl group. In this case, P and Q each is represented by the following general formulae:

$$\begin{array}{c} *-N-** \\ | \\ SO_2-G \end{array} \qquad (R-2)$$

$$\begin{array}{c} *-N-** \\ | \\ CO-G \end{array} \qquad (R-3)$$

wherein * represents the position at which P or Q is connected to B$_1$ or B$_2$; and ** represents the position at which P or Q is connected to one of the free bonds of —(X=Y)$_m$—.

In the above general formulae, the group represented by G is preferably a C$_{1-32}$ group, more preferably a C$_{1-22}$ straight chain, branched or cyclic, saturated or unsaturated, substituted or unsubstituted aliphatic group such as a methyl group, an ethyl group, a benzyl group, a phenoxy group or an isopropyl group, a C$_{6-10}$ substituted or unsubstituted aromatic group such as a phenyl group, a 4-methylphenyl group, a 1-naphthyl group or a 4-dodecyloxyphenyl group, or a 4-membered to 7-membered heterocyclic group comprising nitrogen atoms, sulfur atoms or oxygen atoms as hetero atoms such as a 2-pyridyl group, a 1-phenyl-4-imidazolyl group, a 2-furyl group or a benzothienyl group.

When B$_1$ and B$_2$ each represents a group which can be removed by an alkali (hereinafter referred to as "precursor group"), preferred examples of such a group include hydrolyzable groups such as an acyl group, an alkoxycarbonyl group, an aryloxycarbonyl group, a carbamoyl group, an imidoil group, an oxazolyl group or a sulfonyl group, precursor groups of the type utilizing reverse Michael reaction as described in U.S. Pat. No. 4,009,029, precursor groups of the type utilizing as an intramolecular nucleophilic group an anion produced after ring cleavage reaction as described in U.S. Pat. No. 4,310,612, precursor groups which cause a cleavage reaction by an electron transfer of anions through a conjugated system as described in U.S. Pat. Nos. 3,674,478, 3,932,480 and 3,993,661, precursor groups which cause a cleavage reaction by an electronic transfer of anions which have undergone a reaction after a ring cleavage as described in U.S. Pat. No. 4,335,200, and precursor groups utilizing an imidemethyl group as described in U.S. Pat. Nos. 4,363,865 and 4,410,618.

In the general formula (R-1), P preferably represents an oxygen atom and $B_2$ preferably represents a hydrogen atom. Also, in the general formula (R-1), —(X=Y)$_m$— may form a benzene ring.

Particularly preferred compounds of the general formula (R-1) are represented by the following general formula (R-4) or (R-5):

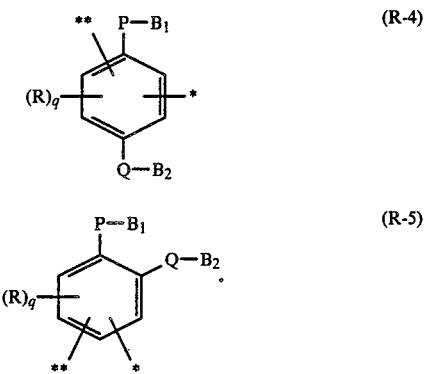

wherein * represents the position at which LVG$_1$—Ball is connected thereto; ** represents the position at which a substituent containing :LIG— is connected thereto, P, Q, $B_1$ and $B_2$ are as defined in the general formula (R-1); R represents a substituent; and q represents an integer of 0 to 2. When q is 2 or more, R may be the same or different. When two R groups are substituents connected to adjacent carbon atoms, they may be connected to each other as divalent groups to represent a cyclic structure. In this case, these R groups form a benzene condensation ring such as naphthalene, benzonorbornene, chroman, indole, benzothiophene, quinoline, benzofuran, 2,3-dihydrobenzofuran, indan or indene. These rings may further contain one or more substituents. However, the number of carbon atoms contained in such substituents is preferably 20 or less.

In the general formula (II), LVG$_1$ is preferably a compound represented by any one of the following general formulae:

*—O—R$_1$—**     (L-1)
*—S—R$_1$—**     (L-2)

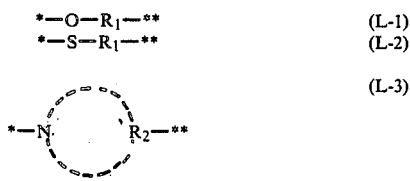

wherein * represents the position at which the compound is connected to A$_1$*; ** represents the position at which the compound is connected to Ball; R$_1$ represents a divalent aromatic group, a divalent aliphatic group or a divalent heterocyclic group; and R$_2$ represents an organic residual group for forming a nitrogen-containing heterocylic group. R$_1$ and R$_2$ may contain substituents besides Ball at any possible position.

In the general formula (II), as Ball there may be used any known diffusion resistant group. The number of carbon atoms contained in Ball is preferably in the range of 8 to 32.

In the general formula (II), SOL represents a dissociating group or a quaternary ammonium salt. Such a dissociating group is preferably a carboxyl group, a sulfo group, a hydroxyl group, a sulfonamide group, a phosphoric acid or a salt thereof. SOL may or may not be used. That is, if :LIG—A$_1$' produced by A$_1$-*—LVG$_1$ bond cleavage during development is sufficiently water-soluble, SOL is not needed.

In the general formula (II), examples of :LIG include ligands described in U.S. Pat. Nos. 4,555,477 and 4,555,478 which have no diffusion resistant groups.

The group represented by :LIP$_1$ preferably contains the following partial structure:

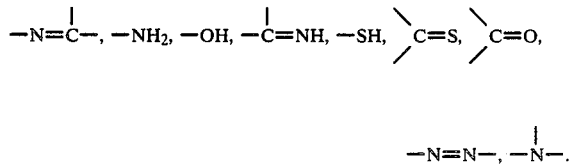

The hetero atoms in these groups (or anions of these dissociated forms) are in such a steric position that they form a chelate with metal ions involving the formation of a 4- to 7-membered ring, preferably a 5-membered or 6-membered ring.

Useful examples of :LIG$_1$ include terpyridine, bipyridine, hydrazone, tetrazolylpyridine, pyridylquinazoline, imine, bisisoquinoline, phenanthroline, bidiazine, pyridyldiazine, pyridylbenzimidazole, phenol, biimidazole, diazyltriazine, o-nitrosoaniline, tetrazine, triazine, oxime, imidazolylpyridine, polypyrrole and hydroxyanthraquinone. These compounds contain at least one of the above mentioned partial structures. These compounds are connected to A directly or through a substituent at possible positions other than the partial structures.

The present compound of the general formula (I) can be used for a multilayer multicolor photographic material having at least three different spectral sensitivities on a support mainly for the purpose of improving image fastness and color reproduction. In general, a multilayer natural color photographic material has at least one red-sensitive emulsion layer, one green-sensitive emulsion layer and one blue-sensitive emulsion layer on a support. The order of arrangement of these layers can be optionally selected. The present compound can be used for any layer such as a high sensitivity layer and a medium sensitivity layer. The present compound can also be used for a light-sensitive silver halide emulsion layer or for its adjacent layers.

The amount of the present compound to be used depends on the structure and usage thereof and is preferably $1 \times 10^{-7}$ to 1.0 mol, particularly preferably $1 \times 10^{-6}$ to 0.5 mol, per mol of silver present in the same layer or its adjacent layers.

The present compound may be used singly or in combination with a known coupler in a layer. If the present compound is used in combination with other color image forming couplers, the molar ratio of the present compound to other color image forming couplers (present compound/other color image forming couplers) is 0.1/99.9 to 90/10, preferably 1/99 to 50/50.
Specific examples of the present compound will be shown hereinafter, but the present invention should not be construed as being limited thereto.
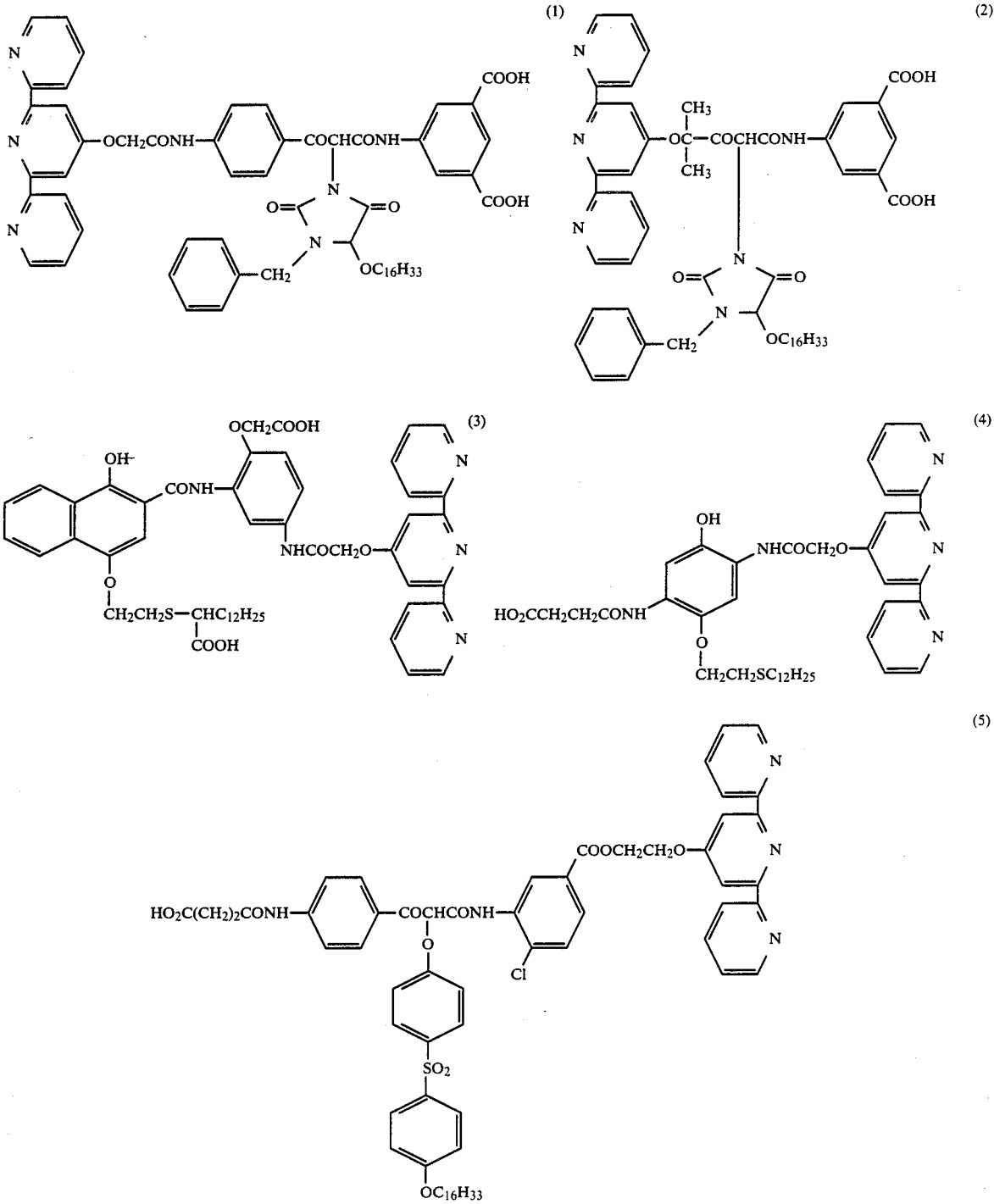

-continued
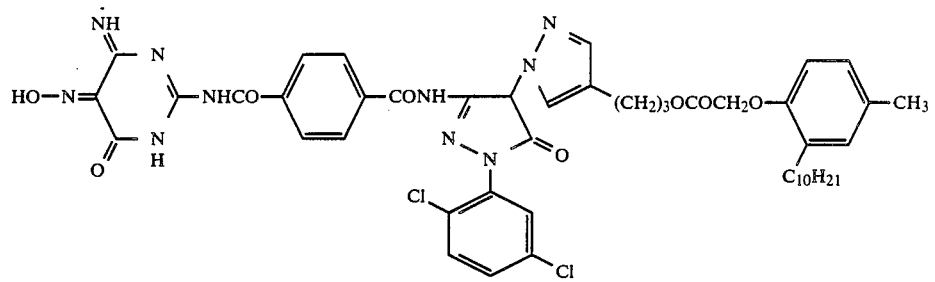 (6)
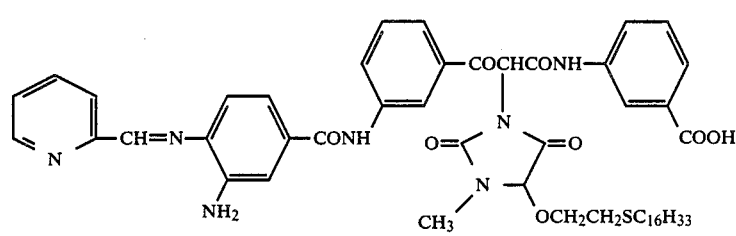 (7)
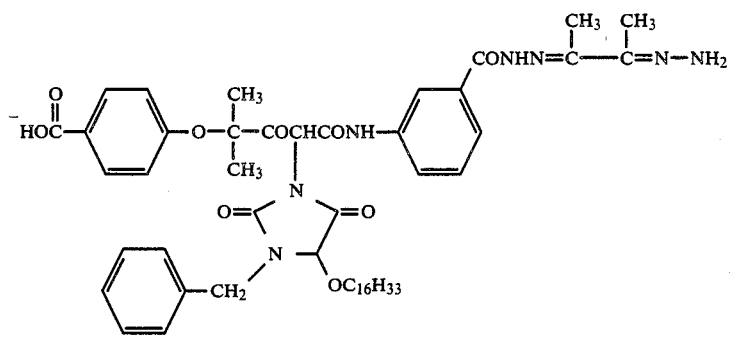 (8)
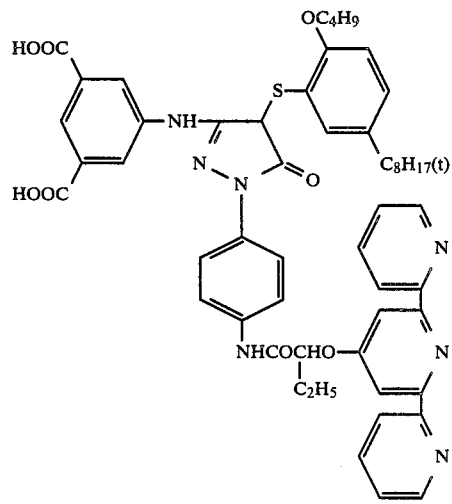 (9)
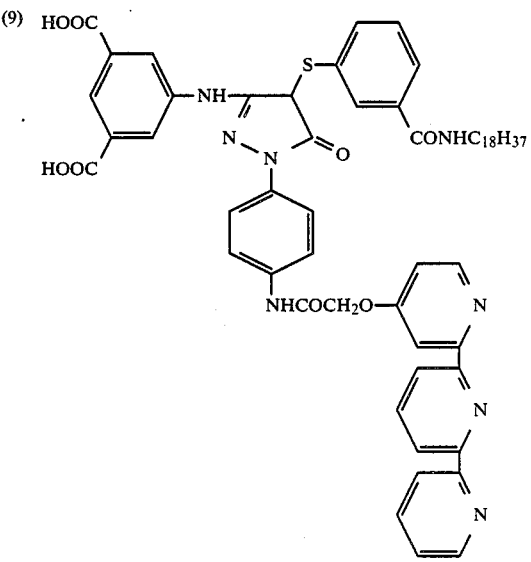 (10)

-continued
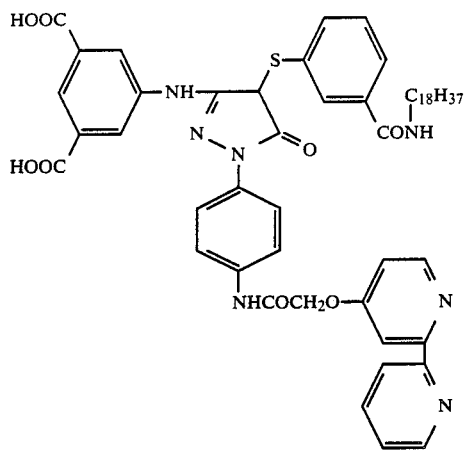
(11)
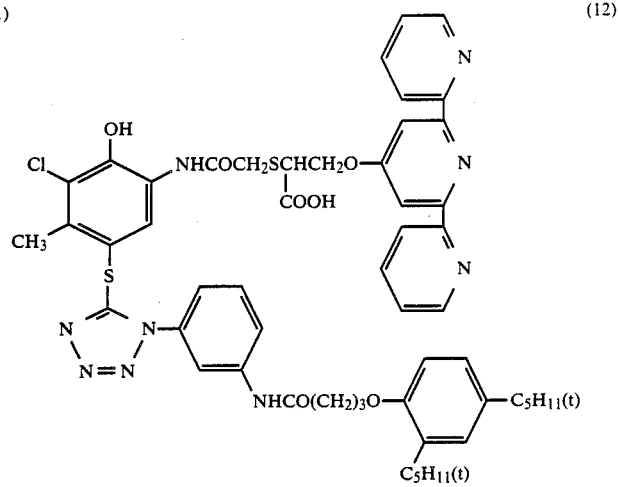
(12)
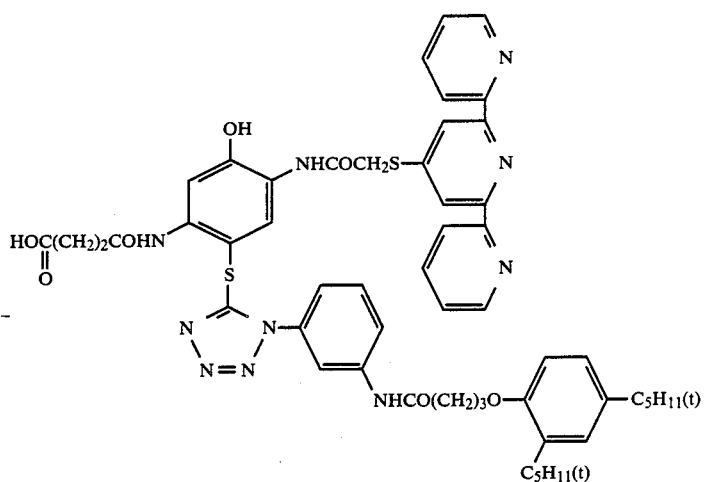
(13)
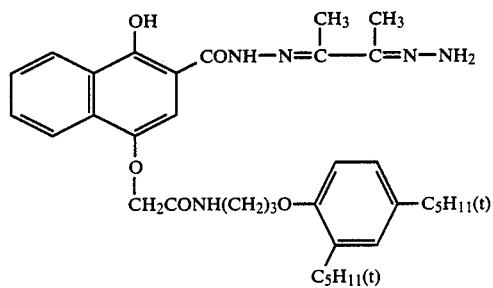
(14)
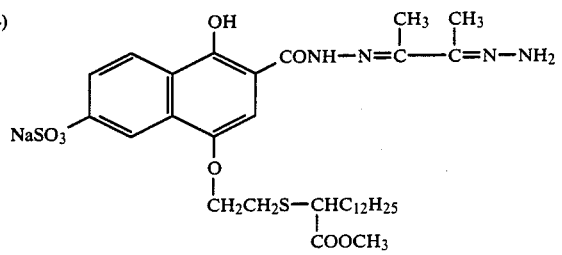
(15)
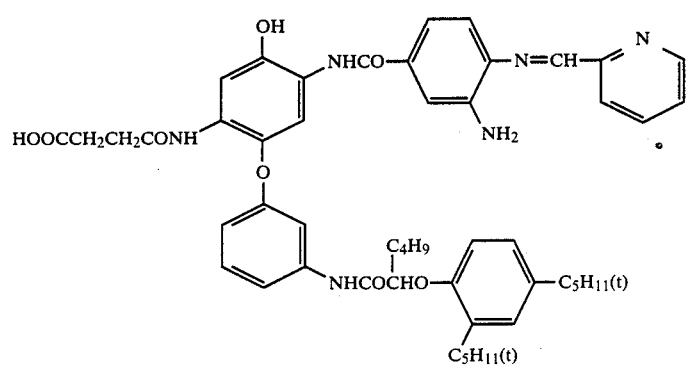
(16)

(17) 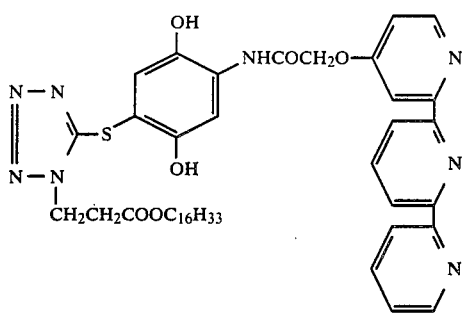
(18) 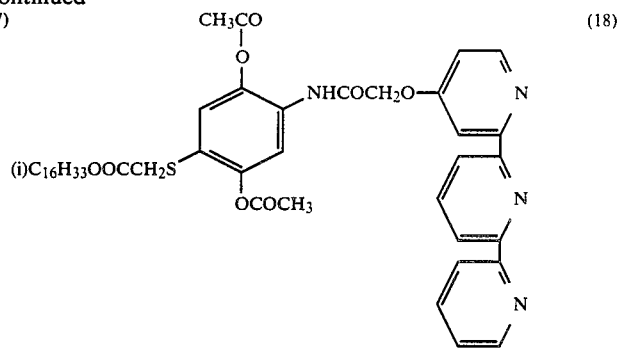
(19) 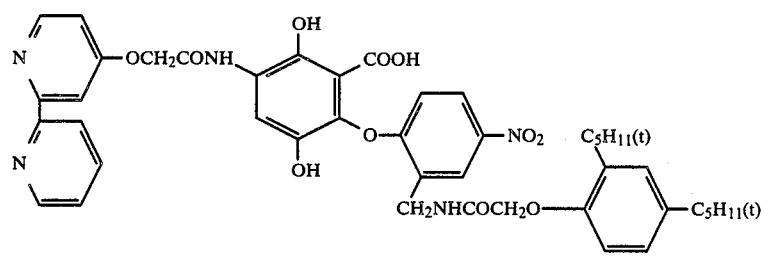
(20) 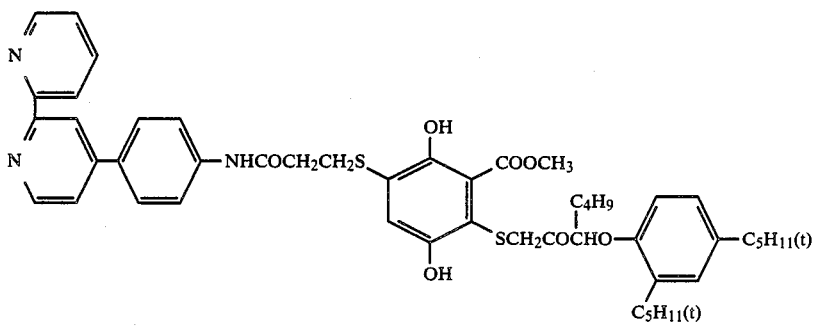
(22) 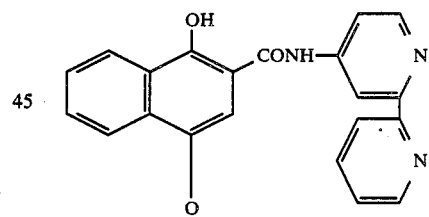
(23) 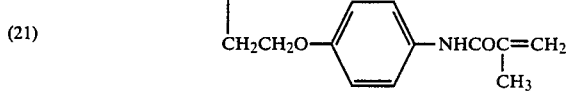
Examples of the present compounds which are monomers are shown hereinafter.
(21) 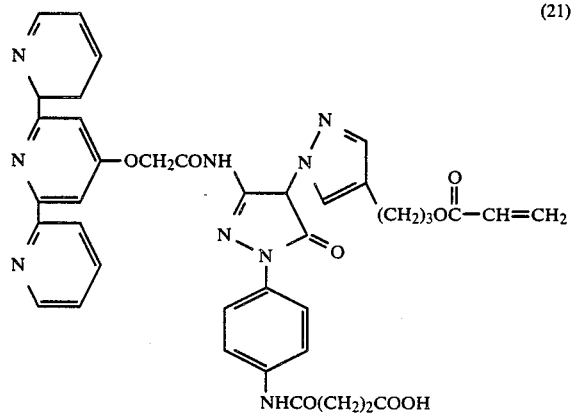
In general, the present compound can be synthesized by any known method. The ligand portion of the present compound can be synthesized by any suitable method as described in *Journal of Organic Chemistry* (Vol. 50, p. 3635, Vol. 47, p. 3027, and Vol. 45, p. 168), *Tetrahedron Letters* (Vol. 23, p. 5291), *Journal of American Chemical Society* (Vol. 107, p. 4647), *Journal of Organic Chemistry* (Vol. 50, p. 2086), and literature cited therein. Many known methods for the preparation of the coupler portion and the oxidation reduction group portion have heretofore been known to be useful.

Specific examples of the synthesis of the present compound will be described hereinafter. The other compounds of the present invention can be similarly synthesized.

SYNTHESIS EXAMPLE 1

Synthesis of Exemplary Compound (1)

Exemplary Compound (1) is synthesized according to the following synthesis process:

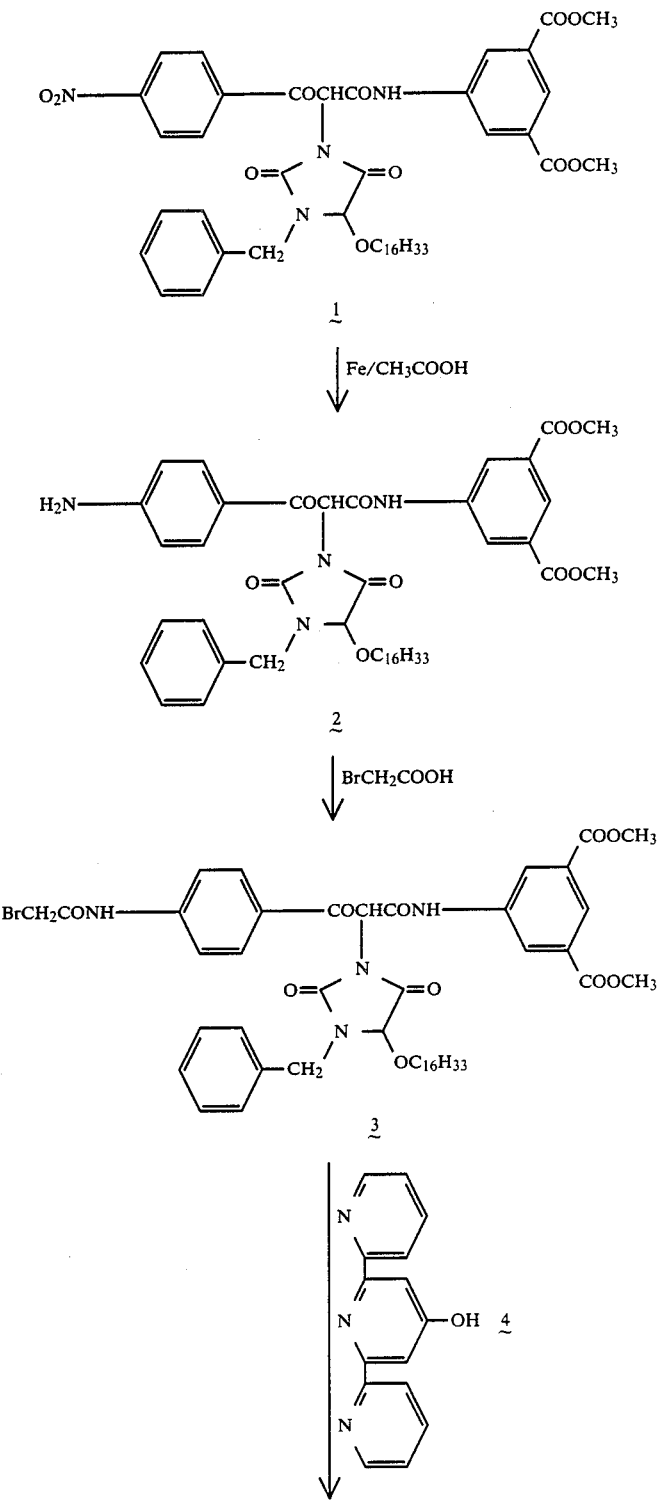

-continued

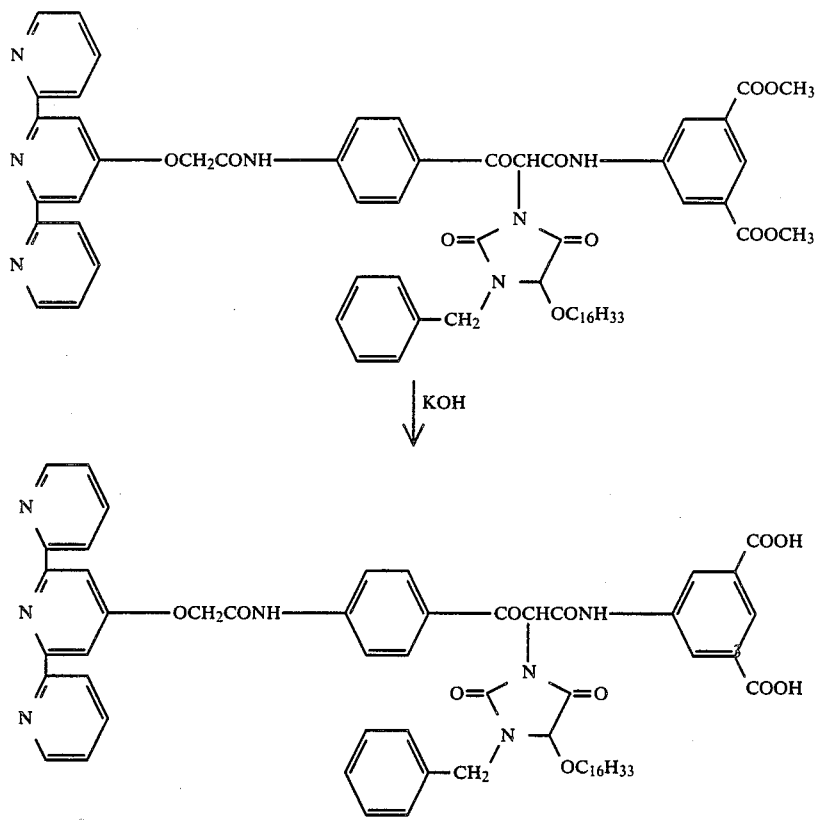

Exemplary Compound (1)

Step 1: Synthesis of 2

30 g of 1 and 30 g of iron powder are added to a mixed solvent of 150 ml of isopropanol, 150 ml of acetic acid and 30 ml of water. The admixture is then heated under reflux for 1 hour. The material thus heated is filtered, and the filtrate is added to water. The resulting crystal is filtered off to obtain 28 g of 2.

Step 2: Synthesis of 3

28 g of 3 and 4.7 g of bromoacetic acid are added to 200 ml of acetonitrile. 7.3 g of N,N'-dicyclohexylcarbodiimide is added to the mixture. The admixture is allowed to undergo reaction for 3 hours. The resulting crystal is filtered off, and the filtrate is concentrated. The residue is recrystallized from a mixed solvent of hexane and ethyl acetate to obtain 21 g of 3.

Step 3: Synthesis of 5

21 of 3, 6 g of 4, and 7 g of tetramethyl guanidine are added to 200 ml of acetonitrile at room temperature. The admixture is stirred at room temperature for 5 hours. The reaction mixture is added to water. The reaction is extracted with ethyl acetate. The resulting oil layer is washed with water, with dilute hydrochloric acid, and then with water. The oil layer is then concentrated. The residue is purified by means of column chromatography to obtain 19 g of 5.

Step 4: Synthesis of Exemplary Compound (1)

19 g of 5 and 5 g of potassium hydroxide are added to a mixed solvent of 120 ml of methanol and 20 ml of water. The admixture is allowed to undergo reaction at room temperature for 2 hours. 500 ml of ethyl acetate and 300 ml of dilute hydrochloric acid are added to the reaction mixture. The reaction mixture is extracted by means of a separatory funnel. The resulting oil layer is concentrated. The residue is crystallized from a mixed solvent of ethyl acetate and hexane to obtain 13 g of the desired Coupler (1).

SYNTHESIS EXAMPLE 2

Synthesis of Exemplary Compound (9)

Exemplary Compound (9) is synthesized according to the following synthesis process:

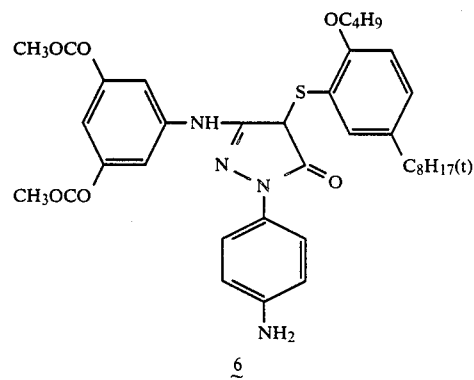

6

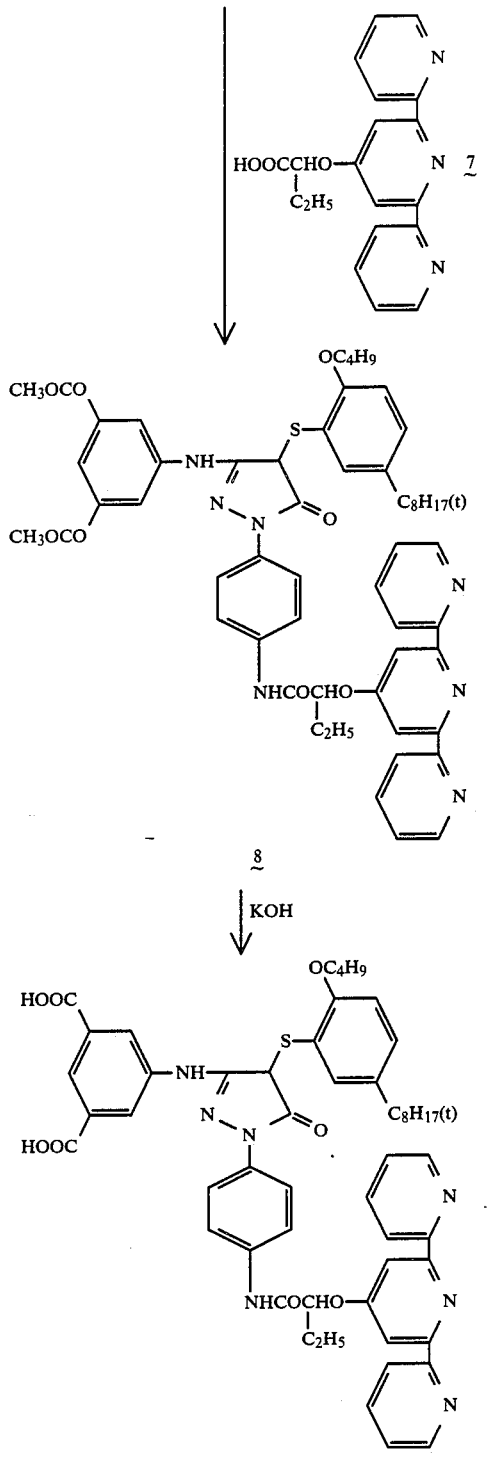

Exemplary Compound (9)

Step 1: Synthesis of 8

30 g of 6 and 14.9 g of 7 are added to 200 ml of N,N'-dimethylformamide. 20 ml of a solution of 9.3 g of N,N'-dicyclohexylcarbodiimide is added dropwise to the admixture at room temperature. The reaction mixture is allowed to undergo reaction for 3 hours. The resulting crystal (N,N'-dicyclohexyl urea) is filtered off, and the filtrate is added to water. An oil layer is extracted with ethyl acetate and washed with water. The oil layer is concentrated. The residue is crystallized from a mixed solvent of acetonitrile and benzene to obtain 28.9 g of 8.

Step 2: Synthesis of Exemplary Compound (9)

28.9 g of 8 is added to a mixed solution of 120 ml of methanol in which 8.2 g of potassium hydroxide is dissolved and 20 ml of water at room temperature. The reaction mixture is then allowed to undergo reaction for 5 hours. The reaction mixture is added to 300 ml of water and neutralized. The resulting crystal is filtered off. The crystal is recrystallized from a mixed solvent of acetonitrile and ethyl acetate to obtain 19.3 g of the desired exemplary Compound (9).

Examples of metal ions which react with the present compound to form a dye include Fe(II), Co(II), Cu(II), Cu(I), Ru(II) and Os(II). The most preferred among these metal ions is Fe(II).

These metal ions are added to the bath both before and after the desilvering step or to a bath provided between the bleach bath and the fixing bath.

Alternatively, these metal ions can be added to a bath having a bleaching capacity to thoroughly effect the formation of a complex. In this case, these metal ions are preferably used to form a complex of $Fe^{2+}$.

The concentration of Fe(II) in the bath containing Fe(II) ions or in the bleach bath is preferably high in the embodiments of the present invention. The minimum amount of Fe(II) necessary for coloring varies with the stability constant of Fe(II) salt added to the processing bath. When the concentration of Fe(II) ions is in the range of $1 \times 10^{-6}$ to 1 mol/l, a substantially sufficient color density can be obtained. The concentration of Fe(II) ions is preferably in the range of $1 \times 10^{-4}$ to 1 mol/l, more preferably in the range of $1 \times 10^{-3}$ to 1 mol/l.

The amount of Fe(II) ions in the bath having a bleaching capacity can be determined by using a metal indicator such as o-phenanthroline.

Examples of bleaching agents which may be used in the present invention include compounds of polyvalent metals such as iron (III), cobalt (III), chromium (VI), and copper (II) (e.g., ferricyanide), peroxides, quinones, nitroso compounds, dichromates, organic complex salts of Fe(III) or Co(III) with an aminopolycarboxylic acid such as ethylenediaminetetraacetic acid, and diethylenetriaminepentaacetic acid, or organic phosphonic acid such as aminopolyphosphonic acid and phosphonocarboxylic acid or organic acid such as citric acid, tartaric acid and malic acid, persulfates, hydrogen peroxide, and permanganates. In view of processing speed and environmental pollution, preferred among these compounds are organic complex salts of Fe(II) and persulfates.

Examples of aminopolycarboxylic acids, aminopolyphosphonic acids or salts thereof which are useful for the formation of organic complex salts of Fe(III) include ethylenediaminetetraacetic acid, diethylenetriaminepentaacetic acid, ethylenediamine-N-(β-oxyethyl)-N,N',N'-triacetic acid, 1,2-diaminopropanetetraacetic acid, triethylenetetraminehexaacetic acid, propylenediaminetetraacetic acid, nitrilotriacetic acid, nitrilotripropionic acid, cyclohexanediaminetetraacetic acid, 1,3-diamino-2-propanoltetraacetic acid, methyliminodiacetic acid, iminodiacetic acid, hydroxyliminodiacetic acid, dihydroxyethylglycine ethyl ether diaminetetraacetic acid, glycol ether diaminetetraacetic acid, ethylenediaminetetrapropionic acid, ethylenediaminedipropioacetic acid, phenylenediaminetetraacetic acid, 2-phosphonobutane-1,2,4-triacetic acid, 1,3-diaminopropanol-N,N,N',N'-tetramethylenephosphonic acid, ethylenediamine-N,N,N',N'-tetramethylenephosphonic acid, 1,3-propylenediamine-N,N,N',N'-tetramethylenephosphonic acid, and 1-hydroxyethylidene-1,1'-diphosphonic acid.

Among these compounds, complex salts of Fe(III) with ethylenediaminetetraacetic acid, diethylenetriaminepentaacetic acid, cyclohexanediaminetetraacetic acid, 1,2-diaminopropanetetraacetic acid, and methyliminodiacetic acid are preferably used because of their high bleaching capacity. In particular, ethylenediaminetetraacetic acid-Fe(III) complex salt has no pollution and storage problems and has been widely put into practical use. From a practical standpoint, a ferric salt of aminopolycarboxylic acid is most preferably used together with a ferrous salt. This combination allows the formation of a complex to be thoroughly effected because there is no increase in the number of processing baths and a rapid processing can be likely attained.

It can be generally determined from electrochemical knowledge that the oxidation state of an aminopolycarboxylic acid-iron complex salt in the bleach bath can be presented by the oxidation reduction potential based on the ratio of the amount of Fe(II) ions to Fe(III) ions.

The inventors have found that the stable presence of Fe(II) ions in the bleach bath can be accomplished by setting the oxidation reduction potential of the bath having a bleaching capacity at 150 mV or less, preferably 120 mV or less, most preferably 100 mV or less, and when the present compound is processed under such a condition, a sufficient color density can be obtained.

The term "oxidation reduction potential" as used herein means a potential measured by a combination of a platinum electrode and a silver chloride electrode at a temperature of 25° C. and pH of 6.0. A high oxidation reduction potential means that the bleaching capacity is strong while the fixing capacity is weak (i.e., there is contained much Fe(III) and little Fe(II)). On the contrary, a low oxidation reduction potential means that the bleaching capacity is weak while the fixing capacity is strong (i.e., there is contained little Fe(III) and much Fe(II)).

The oxidation reduction potential of such a bleach bath can be controlled by controlling the amount of air foam (aeration), allowing the bleaching solution to circulate in the bath without aeration, or mixing the bath with a color developing agent, hydroxylamine, sulfite or the like. These methods are known and examples thereof are described in Japanese Patent Application (OPI) No. 244950/85 (the term "OPI" as used herein refers to a "published unexamined Japanese patent application").

Besides the commonly used bleach bath, a combined bleaching and fixing bath where a fixing process is conducted at the same time may be used as the present bath. Furthermore, processing such as blix may be used after bleaching to speed up the processing.

The present bleaching solution or blix solution may contain a rehaliding agent such as a bromide (e.g., potassium bromide, sodium bromide and ammonium bromide), a chloride (e.g., potassium chloride, sodium chloride and ammonium chloride) and an iodide (e.g., ammonium iodide). There may be optionally added to the present bleaching solution or blix solution one or more organic and inorganic acids having a pH buffering function and alkali metal and ammonium salts thereof such as boric acid, borax, sodium metaborate, acetic acid, sodium acetate, sodium carbonate, potassium carbonate, phosphorous acid, phosphoric acid, sodium phosphate, citric acid, sodium citrate, and tartaric acid, or a corrosion inhibitor such as ammonium nitrate and guanidine.

The suitable amount of a bleaching agent in 1 liter of the present bleaching solution is in the range of 0.1 to 2 mol. The pH value of the present bleaching solution is preferably in the range of 0.5 to 8.0 if a ferric ion complex salt is used. In particular, if a ferric ion complex salt with an aminopolycarboxylic acid, aminopolyphosphonic acid, phosphonocarboxylic acid, or organic phosphonic acid is used, the pH value of the present bleaching solution is preferably in the range of 4.0 to 7.0. If a persulfate is used, the concentration of a bleaching agent in the bleaching solution is preferably in the range of 0.1 to 2 mol/l, and the pH value of the bleaching solution is preferably in the range of 1 to 5.

The fixing agent to be used in the fixing or blix process may include any known fixing agent such as thiosulfate, e.g., sodium thiosulfate and ammonium thiosulfate, thiocyanate, e.g., sodium thiocyanate and ammonium thiocyanate, and water-soluble silver halide solubilizing agent, e.g., thioether compound (ethylene bisthioglycolic acid and 3,6-dithia-1,8-octanediol) and thiourea. These compounds may be used singly or in an admixture. Furthermore, in the blix step, a special blix solution made of a combination of a fixing agent and a large amount of a halide such as potassium iodide as described in Japanese Patent Application (OPI) No. 155354/80 may be used.

In the present fixing or blix step, the concentration of a fixing agent is preferably in the range of 0.2 to 4 mol/l. In the present blix step, the concentration of a ferric ion complex salt is preferably in the range of 0.1 to 2 mol per liter of the blix solution, and the concentration of a fixing agent is preferably in the range of 0.2 to 4 mol per liter of the blix solution. The pH value of the present fixing or blix solution is preferably in the range of 4.0 to 9.0, more preferably in the range of 5.0 to 8.0.

Besides the above additives which may be added to the bleaching solution, there may be added to the present fixing or blix solution a preservative such as sulfite (e.g., sodium sulfite, potassium sulfite, and ammonium sulfite), disulfite, hydroxylamine, hydrazine, and a disulfite-addition product of an aldehyde compound (e.g., acetaldehyde sodium disulfite). Furthermore, the fixing or blix bath may contain various brightening agents, anti-foaming agents, sulface active agents, or organic solvents such as polyvinyl pyrrolidone and methanol.

A bleaching accelerator may be optionally used in the bleaching solution, blix solution and prebath thereof. Specific examples of useful bleaching accelerators include compounds containing a mercapto group or disulfite group as described in U.S. Pat. No. 3,893,858, West German Pat. Nos. 1,290,812 and 2,059,988, Japanese Patent Application (OPI) Nos. 32736/78, 57831/78, 37418/78, 65732/78, 72623/78, 95630/78, 95631/78, 104232/78, 124424/78, 141623/78 and 28426/78, and Research Disclosure, No. 17129 (July, 1978), thiazolidine derivatives as described in Japanese Patent Application (OPI) No. 140129/75, thiourea derivatives as described in Japanese Patent Publication No. 8506/70, Japanese Patent Application (OPI) Nos. 20832/77 and 32735/78, and U.S. Pat. No. 3,706,561, iodides as described in West German Pat. No. 1,127,715 and Japanese Patent Application (OPI) No. 16235/83, polyethylene oxides as described in West German Pat. Nos. 966,410 and 2,748,430, polyamine compounds as described in Japanese Patent Publication No. 8836/70, compounds as described in Japanese Patent Application (OPI) Nos. 42434/74, 59644/74, 94927/78, 35727/79, 26506/80 and 163940/83, and iodine and bromine ions. Among these compounds, the preferably used compounds contain a mercapto group or a disulfide group because of their great acceleration effect. In particular, other preferably used compounds are described in U.S. Pat. No. 3,893,858, West German Pat. No. 1,290,812, and Japanese Patent Application (OPI) No. 95630/78. Furthermore, compounds as described in U.S. Pat. No. 4,552,834 may be preferably used. These bleaching accelerators may be incorporated into the light-sensitive material.

The processing of the present light-sensitive material may be accomplished by any known method or processing solution as described in Research Disclosure, No. 176 (p. 28–30) (RD-17643). This photographic processing may be either silver image forming photographic processing (i.e., black-and-white processing) or color image forming photographic processing (i.e., color photographic processing) depending on the application. The processing temperature can be generally selected between 18° C. and 50° C. However, the processing temperature may be below 18° C. or above 50° C.

The color developing solution used in color development is preferably an alkaline aqueous solution mainly comprising an aromatic primary amine color developing agent. An example of such a color developing agent which may be used is an aminophenol compound. However, a p-phenylenediamine compound is preferably used. Typical examples of such a p-phenylenediamine compound include 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethyl aniline, and sulfates, hydrochlorides, phosphates, p-toluenesulfonates, tetraphenylborates, and p-(t-octyl)benzenesulfonates thereof. These diamines are generally more stable in the form of a salt than in the free state. Therefore, these diamines are preferably used in the form of a salt.

Examples of such an aminophenol derivative include o-aminophenol, p-aminophenol, 4-amino-2-methylphenol, 2-amino-3-methylphenol, and 2-oxo-3-amino-1,4-dimethylbenzene. Besides the above compounds, those described in L. F. A. Mason, Photographic Processing Chemistry, pp. 226–229, Focal Press (1966), U.S. Pat. Nos. 2,193,015 and 2,592,364, and Japanese Patent Application (OPI) No. 64933/73 may be used. Two or more color developing agents may be optionally used in combination.

The present color developing agent may contain a pH buffer such as carbonate, borate and phosphate of alkali metal, a development inhibitor or antifogging agent such as bromide, iodide, benzimidazole, benzothiazole and a mercapto compound, a preservative such as hydroxylamine, triethanolamine, compounds as described in West German Patent Application (OLS) No. 2,622,950, sulfite and disulfite, an organic solvent such as diethylene glycol, a development accelerator such as benzyl alcohol, polyethylene glycol, quaternary ammonium salt, amine, thiocyanate, and 3,6-thiaoctane-1,8-diol, a dye forming coupler, a competing coupler, a nucleating agent such as sodium boron hydride, a development assistant such as 1-phenyl-3-pyrazolidone, a thickening agent, or a chelating agent such as aminopolycarboxylic acid (e.g., ethylenediaminetetraacetic acid, nitrilotriacetic acid, cyclohexanediaminetetraacetic acid, iminodiacetic acid, N-hydroxymethylethylenediaminetriacetic acid, diethylenetriaminepentaacetic acid, triethylenetetraminehexaacetic acid, and compounds as described in Japanese Patent Application (OPI) No. 195845/83), aminophosphonic acid (e.g., 1-hydroxyethylidene-1,1'-diphosphonic acid, organic phosphonic acids as described in Research Disclosure, No. 18170 (May, 1979), aminotris(methylenephosphonic acid), and ethylenediamine-N,N,N',N'-tetramethylenephosphonic acid, and phosphonocarboxylic acids as described in Japanese Patent Application (OPI) Nos. 102726/77, 42730/78, 121127/79, 4024/80, 4025/80, 126241/80, 65955/80, 65956/80 and Research Disclosure, No. 18170 (May, 1979).

Such a color developing agent is generally used in the concentration of about 0.1 g to about 30 g, preferably about 1 g to about 15 g per liter of a color developing solution. The pH value of the color developing solution is generally 7 or more, most generally about 9 to about 13.

In the development of a reversal color light-sensitive material, a black-and-white development is generally followed by a color development. Such a black-and-white developing solution may comprise a dihydroxybenzene such as hydroquinone and hydroquinone monosulfonate, 3-pyrazolidone such as 1-phenyl-3-pyrazolidone, aminophenol such as N-methyl-p-aminophenol, and other known black-and-white developing agents, singly or in combination.

A developing solution used for the black-and-white photographic processing of a photographic light-sensitive material according to the present invention may comprise a known developing agent. Examples of a developing agent which may be used include a dihydroxybenzene such as hydroquinone, a 3-pyrazolidone such as 1-phenyl-3-pyrazolidone, and an aminophenol such as N-methyl-p-aminophenol, singly or in combination.

The developing solution generally may also contain a known preservative, an alkali agent, a pH buffer, and an antifogging agent such as benzotriazole (e.g., methylbenzotriazole and nitroindazole), benzothiazole, indazole, tetrazole and thiazole. The developing solution may optionally further contain a solution assistant, a color toner, a development accelerator, a surface active agent, an anti-forming agent, a water softener, a hardener, and a thickening agent.

The pH value of the developing solution is in the range of 9 to 11, preferably in the range of 9.5 to 10.5.

The fixing solution may use a composition which is commonly used. For instance, the fixing agent may be an organic sulfur compound known to be effective as a fixing agent besides thiosulfates and thiocyanates. The fixing solution may contain a water-soluble aluminum salt as a hardener.

The fixing step or blix step is generally followed by a processing step such as rinsing and stabilization.

The rinsing step and stabilizing step may contain various known compounds for the purpose of either preventing precipitation or stabilizing the rinsing water. Examples of such compounds optionally include a chelating agent such as inorganic phosphoric acid, aminopolycarboxylic acid, and organic phosphonic acid, germicide for preventing generation of various bacteria, algae and mold such as compounds described in *Journal of Anti-Bacterial and Anti-Fungal Agents* (Vol. 11, No. 5, pp. 207–223, 1983) and Hiroshi Mizoguchi ed., *Bokin Bobai no Kagaku*, metal salt such as magnesium salt, aluminum salt, and bismuth salt, alkali metal, ammonium salt, and surface active agent for preventing dry load or unevenness. Alternatively, there may be contained compounds as described in West ed., *Photographic Science and Engineering*, Vol. 6, pp. 344–359 (1965). In particular, a chelating agent or germicide can be effectively used.

In order to save water, the rinsing step is generally effected by means of a multistage countercurrent system consisting of two or more tanks (e.g., 2 to 9 tanks). Furthermore, such a rinsing step may be replaced by a multistage countercurrent stabilizing step as described in Japanese Patent Application (OPI) No. 8543/82. In order to stabilize the image, the present stabilizing bath comprises various compounds besides the above mentioned additives. Typical examples of such compounds include various buffers for adjusting the pH of a film (e.g., to 3 to 9), such as a combination of borate, metaborate, borax, phosphate, carbonate, potassium hydroxide, sodium hydroxide, ammonia water, monocarboxylic acid, dicarboxylic acid, and polycarboxylic acid, and an aldehyde such as formalin. Further, other various additives such as a chelating agent (e.g., inorganic phosphoric acid, aminopolycarboxylic acid, organic phosphonic acid, aminopolyphosphonic acid, and phosphonocarboxylic acid), germicide, anti-mold agent (e.g., thiazole type, isothiazole type, halogenated phenol, sulfanylamide, and benzotriazole), surface active agent, brightening agent, and a metal salt of hardener may be used. These compounds may be used singly or in combination.

Various ammonium salts such as ammonium chloride, ammonium nitrate, ammonium sulfate, ammonium phosphate, ammonium sulfite, and ammonium thiosulfate are preferably used as a film pH adjustor after processing to improve image stability.

For a color light-sensitive material for use in film, the rinsing-stabilizing step which is commonly conducted may be replaced by the above mentioned stabilizing step and rinsing step (for saving water). In this case, if the magenta coupler is a 2-equivalent coupler, formalin in the stabilizing bath may be removed.

The time required for the present rinsing and stabilizing step depends on the type and processing conditions of the light-sensitive material. The value is generally 20 seconds to 10 minutes, preferably 20 seconds to 5 minutes.

The various processing solutions of the present invention are used at a temperature of 10° C. to 50° C. The standard temperature is in the range of 33° C. to 38° C. The processing can be accelerated and shortened by using a higher temperature. In contrast, improvements in image quality and stability of the processing solutions can be accomplished by using a lower temperature. In order to save the amount of silver to be used in the light-sensitive material, a process using cobalt intensification or hydrogen peroxide intensification as described in West German Pat. No. 2,226,770 and U.S. Pat. No. 3,674,499 or a combined development and blix process as described in U.S. Pat. No. 3,923,511 may be used.

The time required for each processing step can be shorter than the standard value as necessary to speed up the processing so far as it gives no adverse effects.

In order to simplify or speed up the processing, the present silver halide color photographic material may comprise a color developing agent or its precursor. Such a color developing agent is preferably used in the form of a precursor because it can improve the stability of the light-sensitive material. Specific examples of such a developing agent precursor include indoaniline compounds as described in U.S. Pat. No. 3,342,597, Shiff base type compounds as described in U.S. Pat. No. 3,342,599, and *Research Disclosure*, Nos. 14850 (August, 1976) and 15159 (November, 1976), aldol compounds as described in *Research Disclosure*, No. 13924, metal complexes as described in U.S. Pat. No. 3,719,492, and urethane compounds as described in Japanese Patent Application (OPI) No. 135628/78. Also, various base type precursors as described in Japanese Patent Application (OPI) Nos. 6235/81, 16133/81, 59232/81, 67842/81, 83734/81, 83735/81, 83736/81, 89735/81, 81837/81, 54430/81, 106241/81, 107236/81, 97531/82 and 83565/82 may be used in the present invention.

In order to accelerate color development, the present silver halide photographic material may comprise various 1-phenyl-3-pyrazolidones. Typical examples of such compounds are described in Japanese Patent Application (OPI) Nos. 64339/81, 144547/82, 211147/82, 50532/83, 50536/83, 50533/83, 50534/83, 505535/83 and 115438/83.

In continuous processing, the fluctuation of the composition of each processing solution can be prevented by filling up the processing solutions so that a constant finish can be provided. The amount of each processing solution to be supplied may be reduced to half or less of the standard value for the purpose of saving cost or other like purposes.

Each processing bath can be optionally provided with a heater, temperature sensor, liquid level sensor, circulating pump, filter, various floating cover, or various squeegees.

The photographic emulsion layer in the present photographic light-sensitive material may comprise any silver halide selected from silver bromide, silver iodobromide, silver iodochlorobromide, silver chlorobromide and silver chloride. A preferred silver halide is silver iodobromide or silver iodochlorobromide containing about 30 mol% or less silver iodide. A particularly preferred silver halide is silver iodobromide containing about 2 mol% to about 25 mol% of silver iodide.

The particulate silver halide in the photographic emulsion may be in the form of a so-called regular particle having a regular crystal shape such as cube, octahedron, and tetradecahedron, an irregular particle having an irregular shape such as sphere, a particle having a crystal defect such as twinning plane, or a composite thereof.

The particulate silver halide may be fine particles having a diameter of about 0.1 μm or less or may be large particles having a particle size of up to about 10 μm (diameter of projected area). The present particulate silver halide may be in the form of a monodispersed emulsion having a narrow distribution or a polydispersed emulsion having a wide distribution.

The silver halide photographic emulsion which can be used in the present invention can be prepared by any known method such as those described in *Research Disclosure*, No. 17643 (December, 1978), pp. 22–23, "I. Emulsion Preparation and Types" and *Research Disclosure*, No. 18716 (November, 1979), p. 648.

The photographic emulsion to be used in the present invention can be prepared by any suitable method as described in P. Glafkides, *Chimie et Physique Photogra-*

*phique* (Paul Montel, 1967), G. F. Duffin, *Photographic Emulsion Chemistry* (Focal Press, 1966), and V. L. Zelikman et al., *Making and Coating Photographic Emulsion* (Focal Press, 1964). Thus, an acidic process, a neutral process or an ammonia process may be used. The reaction of a soluble silver salt with a soluble halogen salt may be effected by a single jet process, double jet process or a combination thereof. A process in which particles are formed in excess silver ions (so-called reversal mixing process) can be used. One form of the double jet process is a so-called controlled double jet process in which the pAg of the liquid phase in which a silver halide is formed is kept constant. By this method, an emulsion of particulate silver halide having a regular crystal shape and a nearly uniform particle size can be obtained.

Alternatively, two or more silver halide emulsions which have been separately prepared may be mixed with each other to form a desired silver halide emulsion.

An emulsion of particulate silver halide having the above mentioned regular crystal shape can be obtained by controlling the pAg and pH of the liquid phase in which the particles are being formed. Details of such a process are described in *Photographic Science and Engineering* (Vol. 6. pp. 159–165, 1961), *Journal of Photographic Science* (Vol. 12, pp. 242–251, 1964), U.S. Pat. No. 3,655,394 and British Pat. No. 1,413,748.

A typical example of the above mentioned mono-dispersed emulsion is an emulsion of particulate silver halide having an average diameter of more than about 0.1 μm and a distribution of particle diameter in which at least about 95% by weight of the particles is within ±40% of the average particle diameter. In the present invention, an emulsion of particulate silver halide having an average diameter of about 0.25 to 2 μm and a distribution of particle diameter in which at least about 95% by weight or number of the particles is within ±20% of the average particle diameter can be used. Examples of preparation methods of such an emulsion are described in U.S. Pat. Nos. 3,574,628 and 3,655,394 and British Pat. No. 1,413,748. Alternatively, there may be preferably used in the present invention monodispersed emulsions as described in Japanese Patent Application (OPI) Nos. 8600/73, 39027/76, 83097/76, 137133/78, 48521/79, 99419/79, 37635/83 and 49938/83.

Furthermore, tabular particles having an aspect ratio of about 5 or more can be used in the present invention. Such tabular particles can be easily prepared by any suitable method as described in Gutoff, *Photographic Science and Engineering*, Vol. 14, pp. 248–257 (1970), U.S. Pat. Nos. 4,434,226, 4,414,310, 4,433,048, 4,439,520 and British Pat. No. 2,112,157. If such tabular particles are used, advantages such as improvements in the color sensitization efficiency by a sensitizing dye, graininess and sharpness can be attained. This fact is described in detail in U.S. Pat. No. 4,434,226.

The crystal structure may consist of a uniform halogen composition or may be such that the inside and the outside thereof are different from each other in halogen composition. Alternatively, the crystal structure may be present in layers. Examples of such emulsion particles are disclosed in British Pat. No. 1,027,146, U.S. Pat. Nos. 3,505,068 and 4,444,877, and Japanese Patent Application (OPI) No. 248469/83. In a crystal structure, silver halides having different compositions may be connected to each other by an epitaxial junction. Alternatively, a silver halide may be connected to a compound other than silver halide, such as a silver thiocyanate and an oxide salt. Examples of such emulsion particles are disclosed in U.S. Pat. Nos. 4,094,684, 4,142,900 and 4,459,353, British Pat. No. 2,038,792, U.S. Pat. Nos. 4,349,622, 4,395,478, 4,433,501, 4,463,087, 3,656,962 and 3,852,067, and Japanese Patent Application (OPI) No. 162540/84.

Alternatively, a mixture of particles having various crystal shapes may be used.

In general, the present emulsion is subjected to chemical ripening and spectral sensitization after physical ripening. Examples of additives used in such processes are described in *Research Disclosure*, Nos. 17643 and 18716. Furthermore, these descriptions are shown in the table below. In addition, examples of known photographic additives which may be used in the present invention are described in the above two literature articles. The places where these descriptions are made are also shown in the table below.

| Type of Additives | RD 17643 | RD 18716 |
|---|---|---|
| 1. Chemical Sensitizer | Page 23 | Page 648, right column |
| 2. Sensitivity Improver | | " |
| 3. Spectral Sensitizer, Supersensitizer | | Page 648, right column to page 649, right column |
| 4. Brightening Agent | Page 24 | |
| 5. Antifogging Agent and Stabilizer | Pages 24–25 | Page 649, right column |
| 6. Light Absorber, Filter Dye, Ultraviolet Absorber | Pages 25–26 | Page 649, right column to page 650, left column |
| 7. Stain Inhibitor | Page 25 right column | Page 650, right column to left column |
| 8. Dye Image Stabilizer | Page 25 | |
| 9. Hardener | Page 26 | Page 651, left column |
| 10. Binder | Page 26 | " |
| 11. Plasticizer, Lubricant | Page 27 | Page 650, right column |
| 12. Coating Assistant, Surface Active Agent | Pages 26–27 | " |
| 13. Antistatic Agent | Page 27 | " |

In the present invention, various color couplers can be used. Specific examples of these color couplers are described in patents cited in *Research Disclosure*, No. 17643 (VII-C to G). Important dye forming couplers are couplers which produce subtractive primaries, i.e., yellow, magenta and cyan upon color development. Other specific diffusion resistant 4- or 2-equivalent couplers discussed below may be preferably used instead of the couplers described in the patents cited in *Research Disclosure*, No. 17643 (VII-C and D).

A typical example of a yellow coupler which may be used in the present invention is a hydrophobic acylacetamide coupler containing a ballast group. Specific examples of such a yellow coupler are described in U.S. Pat. Nos. 2,407,210, 2,875,057 and 3,265,506. In the present invention, a 2-equivalent yellow coupler is preferably used. Typical examples of such a 2-equivalent yellow coupler include yellow couplers having a coupling-off group containing an oxygen atom as a coupling-off atom as described in U.S. Pat. Nos. 3,408,194, 3,447,928, 3,933,501 and 4,022,620, and yellow couplers having a coupling-off group containing a nitrogen atom as a coupling-off atom as described in Japanese Patent Publication No. 10739/83, U.S. Pat. Nos. 4,401,752 and 4,326,024, *Research Disclosure*, No. 18053 (April, 1979), British Pat. No. 1,425,020, West German Patent Application (OLS) Nos. 2,219,917, 2,261,361, 2,329,587 and 2,433,812. α-Pivaloylacetanilide couplers are excellent in fastness of the color forming dye, particularly to light. On the other hand, α-benzoylacetanilide couples can provide a high color density.

An example of a magenta coupler which can be used in the present invention is a hydrophobic indazolone or cyanoacetyl, preferably a 5-pyrazolone and a pyrazoloazole coupler containing a ballast group. In view of the hue of the color forming dye or color density, a 5-pyrazolone coupler may be preferably used as such a coupler whose 3-position is substituted by an arylamino or acylamino group. Typical examples of such a coupler are described in U.S. Pat. No. 2,311,082, 2,343,703, 2,600,788, 2,908,573, 3,062,653, 3,152,896 and 3,936,015. A particularly preferable coupling-off group for the 2-equivalent 5-pyrazolone coupler is a coupling-off group containing a nitrogen atom as a coupling-off atom as described in U.S. Pat. No. 4,310,619, or an arylthio group as described in U.S. Pat. No. 4,351,897. A 5-pyrazolone coupler containing a ballast group as described in European Pat. No. 73,636 can provide a high color density. An example of such a pyrazoloazole coupler which may be used include a pyrazolobenzimidazole as described in U.S. Pat. No. 3,061,432. Preferred example of such a pyrazoloeazole coupler include pyrazolo[5,1-c][1,2,4]-triazoles as described in U.S. Pat. No. 3,725,967, pyrazolotetrazoles as described in *Research Disclosure*, No. 24220 (June, 1984) and Japanese Patent Application (OPI) No. 33552/85, and pyrazoloazoles as described in *Research Disclosure, No.* 24230 (June 1984) and Japanese Patent Application (OPI) No. 43659/85. Imidazo[1,2-b]pyrazoles as described in U.S. Pat. No. 4,500,630 are preferably used because they have small amounts of yellow side absorption by a color forming dye and they also have an excellent fastness to light. Pyrazolo[1,5-b][1,2,4]triazoles as described in U.S. Pat. No. 4,540,654 are particularly preferred.

An example of a cyan coupler which may be used in the present invention is a hydrophobic diffusion resistant naphthol or phenol couplers. An example of such a cyan coupler which may be used includes a naphthol coupler as described in U.S. Pat. No. 2,474,293. Typical examples of preferred cyan couplers include 2-equivalent naphthol couplers having a coupling-off group containing an oxygen atom as a coupling-off atom as described in U.S. Pat. Nos. 4,052,212, 4,146,396, 4,228,233 and 4,296,200. Specific examples of phenol couplers are described in U.S. Pat. Nos. 2,369,929, 2,801,171, 2,772,162 and 2,895,826.

Couplers which can form a cyan dye which is fast or resistant to moisture and heat are preferably used in the present invention. Typical examples of such couplers include phenol cyan couplers containing an ethyl group or a higher alkyl group in the meta-position of the phenol nucleus as described in U.S. Pat. No. 3,772,002, 2,5-diacylamino-substituted phenol couplers as described in U.S. Pat. Nos. 2,772,162, 3,758,308, 4,126,396, 4,334,011 and 4,327,173, West German Patent Application (OLS) No. 3,329,729, and European Pat. No. 121,365, and phenol couplers containing a phenylureido group in the 2-position and an acylamino group in the 5-position as described in U.S. Pat. Nos. 3,446,622, 4,333,999, 4,451,559 and 4,427,767. Cyan couplers having the 5-position of a naphthol substituted by a sulfonamide group, an amide group or the like as described in European Patent 161,626A are also excellent in fastness of color image and thus can be preferably used in the present invention.

In order to correct unnecessary absorption by a color forming dye, a color light-sensitive material for camera use preferably may comprise a colored coupler other than those of the present invention to effect masking. Typical examples of such a colored coupler include yellow colored magenta couplers as described in U.S. Pat. No. 4,163,670 and Japanese Patent Publication No. 39413/82, and magenta colored cyan couplers as described in U.S. Pat. Nos. 4,004,929 and 4,138,258 and British Pat. No. 1,146,368. Other color couplers are described in *Research Disclosure*, No. 17643 (VII-G).

The graininess can be improved by using a coupler whose color forming dye has a proper diffusibility. Specific examples of such a magenta coupler are described in U.S. Pat. No. 4,366,237 and British Pat. No. 2,125,570. Specific examples of such a yellow, magenta or cyan coupler are described in European Pat. No. 96,570 and West German Patent Application (OLS) No. 3,234,533.

The above mentioned dye forming couplers and special couplers may form a dimer or higher polymer. Typical examples of polymerized dye forming couplers are described in U.S. Pat. Nos. 3,451,820 and 4,080,211. Specific examples of polymerized magenta couplers are described in British Pat. No. 2,102,173 and U.S. Pat. No. 4,367,282.

Couplers which release a photographically useful residual group upon coupling may be preferably used in the present invention. Examples of DIR couplers which release a development inhibitor and may be effectively used are described in *Research Disclosure*, No. 17643 (VII-F).

Examples of couplers which may be preferably used in combination with the present couplers include a developer deactivation type coupler as described in Japanese Patent Application (OPI) No. 151944/82, a timing type coupler as described in U.S. Pat. No. 4,248,962 and Japanese Patent Application (OPI) No. 154234/82, and a reaction type coupler as described in Japanese Patent Application (OPI) No. 184248/85. Particularly preferred examples of couplers which may be used in combination with the present couplers include developer deactivation type DIR couplers as described in Japanese Patent Application (OPI) Nos. 151944/82, 217932/83, 218644/85, 225156/85 and 233650/85, and reaction type DIR couplers as described in Japanese Patent Application (OPI) No. 184248/85.

The present light-sensitive material may comprise a coupler which releases a nucleating agent or development accelerator or its precursor imagewise upon development. Specific examples of such compounds are described in British Pat. Nos. 2,097,140 and 2,131,188. Couplers which release a nucleating agent having a function to absorb silver halide are particularly preferred. Specific examples of such couplers are described in Japanese Patent Application (OPI) Nos. 157638/84 and 170840/84.

Examples of proper supports which may be used in the present invention are described on page 28 of *Research Disclosure*, No. 17643 and right column on page 647 to left column on page 648 of *Research Disclosure*, No. 18716.

The present compounds and the above mentioned couplers may be incorporated in the light-sensitive material by various known dispersion methods such as a solid dispersion process, an alkali dispersion process, a latex dispersion process, and an oil-in-water dispersion process. Preferred among these dispersion processes is the latex dispersion process. The oil-in-water dispersion process is more preferably used among these processes. In the oil-in-water dispersion process, the present compound or coupler is dissolved in either a high boiling organic solvent having a boiling point of 175° C. or above or in a so-called auxiliary solvent having a lower boiling point or in a mixed solvent thereof. The resulting solution is then finely dispersed in water or in an aqueous medium such as a gelatin aqueous solution in the presence of a surface active agent. Examples of such a high boiling organic solvent are described in U.S. Pat. No. 2,322,027. The dispersion may involve phase reversal of the emulsion. The auxiliary solvent may be optionally removed or reduced by distillation, noodle rinsing or ultrafiltration before the emulsion is coated on a support.

Specific examples of such a high boiling solvent include phthalic esters such as dibutyl phthalate, dicyclohexyl phthalate, di-2-ethylhexyl phthalate, and decyl phthalate, phosphoric or phosphonic esters such as triphenyl phosphate, tricresyl phosphate, 2-ethylhexyl diphenyl phosphate, tricyclohexyl phosphate, tri-2-ethylhexyl phosphate, tridecyl phosphate, tributoxyethyl phosphate, trichloropropyl phosphate, and di-2-ethylhexylphenyl phosphate, benzoic esters such as 2-ethylhexyl benzoate, dodecyl benzoate, and 2-ethylhexyl-p-hydroxy benzoate, amides such as diethyldodecanamide and N-tetradecyl pyrrolidone, alcohols or phenols such as isostearyl alcohol and 2,4-di-tert-amylphenol, aliphatic carboxylic esters such as dioctyl azelate, glycerol tributylate, isostearyl lactate, and trioctyl citrate, aniline derivatives such as N,N-dibutyl-2-butoxy-5-tert-octyl aniline, and hydrocarbons such as paraffin, dodecylbenzene, and diisopropyl naphthalene. A suitable auxiliary solvent which may be used includes an organic solvent having a boiling point of about 30° C. or above, preferably 50° C. to about 160° C. Typical examples of such an organic solvent include ethyl acetate, butyl acetate, ethyl propionate, methyl ethyl ketone, cyclohexanone, 2-ethoxyethyl acetate, and dimethylformamide.

Specific examples of the procedures and the effects of the latex dispersion process and latexes used for impregnation are described in U.S. Pat. No. 4,199,363, and West German Patent Application (OLS) Nos. 2,541,274 and 2,541,230.

The present invention will be further illustrated in the following examples, but the present invention should not be construed as being limited thereto.

EXAMPLE 1

Specimen 101 is prepared by providing on a support of a triacetyl cellulose film a color light-sensitive material consisting of various layers of the following compositions:

First Layer: Emulsion Layer

| Silver iodobromide emulsion (silver iodide: 5 mol %) (as calculated in terms of amount of silver) | 1.0 g/m² |
| --- | --- |
| Coupler C-3 | 0.6 g/m² |
| Coupler B-1 | 0.77 g/m² |
| Sensitizing Dye I | 2 × 10⁻⁴ g/m² |
| Sensitizing Dye II | 6 × 10⁻⁴ g/m² |
| Sensitizing Dye III | 2 × 10⁻⁵ g/m² |
| Oil-1 | 0.5 cc/m² |

-continued

| Oil-2 | 0.5 cc/m² |
| --- | --- |

Second Layer: Protective Layer

A gelatin layer containing particulate trimethyl methacrylate (particle diameter: 1.5 μm).

Besides the above compositions, Gelatin Hardener H-1 and a surface active agent are added to each layer.

The above specimen is prepared by using the following compounds:

Coupler C-3

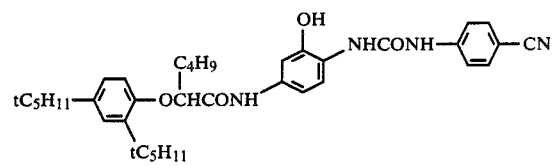

Coupler B-1 (compound described in U.S. Pat. No. 4,555,477)

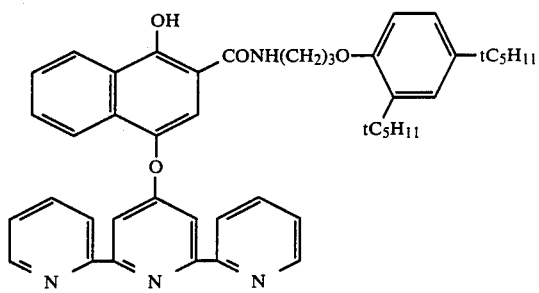

Coupler C-2

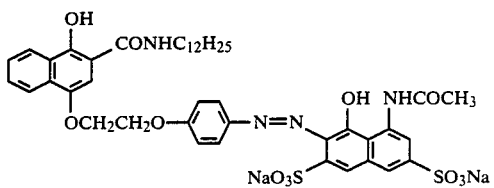

Oil-1 Tricresyl Phosphate
Oil-2 Dibutyl Phthalate
Coupler C-7

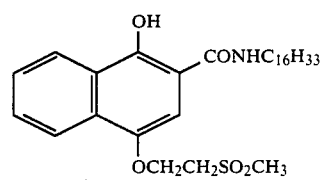

Sensitizing Dye I

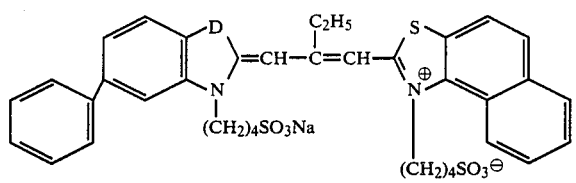

Sensitizing Dye II

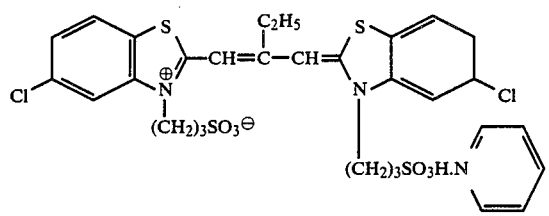

Sensitizing Dye III

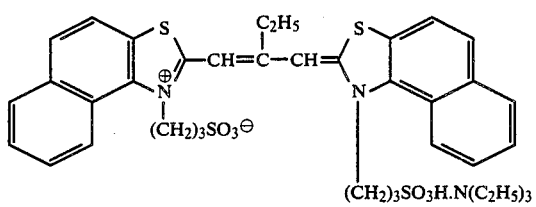

Preparation of Specimens 102 to 105

Couplers shown in Table 1 are used instead of Coupler B-1 for Specimen 101. However, for Specimens 103 to 105, equimolecular amounts of Coupler C-7 are further added to make gradation thereof substantially level with each other.

Specimens 101 to 105 thus obtained are subjected to wedgewise exposure to light with 20 CMS from a tungsten lamp whose color temperature has been adjusted to 4,800° K. through a yellow filter. The specimens thus exposed are then subjected to the following processing steps:

| Color Development | 2 min 10 sec |
|---|---|
| Bleaching | 6 min 30 sec |
| Rinsing | 2 min 10 sec |
| Iron (II) Bath | 6 min 30 sec |
| Rinsing | 2 min 10 sec |
| Fixing | 4 min 20 sec |
| Rinsing | 3 min 15 sec |
| Stabilizing | 1 min 05 sec |

The composition of the processing solutions used in these steps were as follows:

Color Developing Solution:

| Diethylenetriaminepentaacetic Acid | 1.0 g |
|---|---|
| 1-Hydroxyethylidene-1,1-diphosphonic Acid | 2.0 g |
| Sodium Sulfite | 4.0 g |
| Potassium Carbonate | 30.0 g |
| Potassium Bromide | 1.4 g |
| Potassium Iodide | 1.3 mg |
| Hydroxylamine Sulfate | 2.4 g |
| 4-(N—Ethyl-N—β-hydroxyethylamino)-2-methylaniline Sulfate | 4.5 g |
| Water to make | 1.0 l |

-continued

| pH | 10.0 |
|---|---|

Bleaching Solution:

| Ammonium Ethylenediaminetetraacetato Ferrate | 100.0 g |
|---|---|
| Disodium Ethylenediaminetetraacetate | 10.0 g |
| Ammonium Bromide | 150.0 g |
| Ammonium Nitrate | 10.0 g |
| Water to make | 1.0 l |
| pH | 6.0 |

Iron (II) Bath:

| Ferrous Ammonium Sulfate | $1 \times 10^{-2}$ mol |
|---|---|
| Water to make | 1.0 l |
| pH | 6.0 |

Fixing Solution:

| Disodium Ethylenediaminetetraacetate | 1.0 g |
|---|---|
| Sodium Sulfite | 4.0 g |
| Aqueous Solution of Ammonium Thiosulfate (70%) | 175.0 ml |
| Sodium Bisulfite | 4.6 g |
| Water to make | 1.0 l |
| pH | 6.6 |

Stabilizing Solution:

| Formalin (40%) | 2.0 ml |
|---|---|
| Polyoxyethylene-p-monononylphenyl Ether (average polymerization degree: approx. 10) | 0.3 g |
| Water to make | 1.0 l |

The results are shown in Table 1.

Table 1 shows that when the present compound is used, a reduction in sensitivity as seen in the case of conventional colored couplers is not caused and a great masking effect can be obtained, thus improving coupling activity.

TABLE 1

| Specimen No. | Masking Coupler | Amount Added | Sensitivity* | Masking** |
|---|---|---|---|---|
| 101 (Comparison) | B-1 | Control | ±0 (control) | 0.1 |
| 102 (Comparison) | C-2 | ⅓ time mol | −0.15 | 0.4 |
| 103 (Invention) | (1) | Equimolecular | +0.02 | 0.35 |
| 104 (Invention) | (3) | Equimolecular | +0.03 | 0.4 |
| 105 (Invention) | (9) | Equimolecular | +0.02 | 0.25 |

*Log E of the point where fog + density 0.2 (control = 0)
**Reduction in magenta density by fogging portion at log E which gives cyan density 1.0.

EXAMPLE 2

Specimens 101 to 105 prepared in Example 1 are subjected to the same exposure to light as used in Example 1 and then to a process containing the following combined bleaching and fixing solution.

During processing, the concentration of iron (II) is measured by the above mentioned method. As a result, it was found that iron (II) is present in an amount of 5 mol% ($1\times10^{-2}$ mol/l) of total iron salts.

The results are shown in Table 2.

As in Example 1, the reduction in sensitivity is extremely low and the masking effect is great.

Thus, the objects of the present invention are thoroughly attained.

Processing Step:

| Color Development | 3 min 15 sec | 38° C. |
|---|---|---|
| Blix | 1 min 40 sec | " |
| Stabilizing | 40 sec | " |

Preparation of Processing Solution
Color Developer:

| Diethylenetriaminepentaacetic Acid | 1.0 g |
|---|---|
| 1-Hydroxyethylidene-1,1-diphosphonic Acid | 2.0 g |
| Sodium Sulfite | 4.0 g |
| Potassium Carbonate | 30.0 g |
| Potassium Bromide | 1.4 g |
| Potassium Iodide | 1.3 mg |
| Hydroxylamine Sulfate | 2.4 g |
| 4-(N—Ethyl-N—β-hydroxyethylamino)-2-methylaniline Sulfate | 4.5 g |
| Water to make | 1 l |
| pH | 10.00 |

Blix Solution:

| Ammonium Ethylenediaminetetraacetato Ferrate | 80.0 g |
|---|---|
| Disodium Ethylenediaminetetraacetate | 10.0 g |
| Bleaching Accelerator BA-1 | 1.5 g |

BA-1

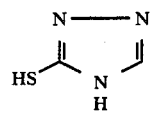

| Sodium Sulfite | 12.0 g |
|---|---|
| Aqueous Solution of Ammonium Thiosulfate (70%) | 240 ml |
| Water to make | 1 l |
| Ammonia water (28%) to make pH to | 6.8 |

Rinsing Solution:

| Disodium Ethylenediaminetetraacetate | 0.4 g |
|---|---|
| Water to make | 1 l |
| Sodium hydroxide to make pH to | 7.0 |

Stabilizing Solution:

| Formalin (37% w/v) | 2.0 ml |
|---|---|
| Polyoxyethylene-p-monononylphenyl Ether (average polymerization degree: 10) | 0.3 g |
| Water to make | 1 l |

TABLE 2

| Specimen No. | Sensitivity | Masking |
|---|---|---|
| 101 (Comparison) | ±0 (control) | 0.05 |
| 102 (Comparison) | −0.14 | 0.38 |
| 103 (Invention) | ±0 | 0.25 |
| 104 (Invention) | −0.02 | 0.3 |

TABLE 2-continued

| Specimen No. | Sensitivity | Masking |
|---|---|---|
| 105 (Invention) | −0.02 | 0.25 |

EXAMPLE 3

Specimen 301 is prepared by providing on an undercoated support of a cellulose triacetate film a multilayer color light-sensitive material containing various layers of the following compositions:

Composition of Light-Sensitive Layer

The coated amount is represented in terms of the amount of silver (g/m$^2$) for silver halide and colloidal silver. The coated amount of coupler and additive is represented in g/m$^2$. The coated amount of sensitizing dye is represented in terms of the molar number per mol of silver halide in the same layer.

First Layer: Antihalation Layer

| Black colloidal silver | 0.2 |
|---|---|
| Gelatin | 1.3 |
| Colored Coupler C-1 | 0.06 |
| Ultraviolet Absorber UV-1 | 0.1 |
| Ultraviolet Absorber UV-2 | 0.2 |
| Dispersing oil, Oil-1 | 0.01 |
| Dispersing oil, Oil-2 | 0.01 |

Second Layer: Intermediate Layer

| Silver iodobromide emulsion (silver iodide: 2 mol %, average particle diameter: 0.3 μm) | 0.4 (silver) |
|---|---|
| Gelatin | 0.6 |
| Sensitizing Dye I | $1.0 \times 10^{-4}$ |
| Sensitizing Dye II | $3.0 \times 10^{-4}$ |
| Sensitizing Dye III | $1 \times 10^{-5}$ |
| Coupler C-3 | 0.06 |
| Coupler C-4 | 0.06 |
| Coupler C-2 | 0.03 |
| Dispersing oil, Oil-1 | 0.03 |
| Dispersing oil, Oil-3 | 0.012 |

Third Layer: First Red-Sensitive Emulsion Layer

| Silver iodobromide emulsion (silver iodide: 2 mol %, average particle diameter: 0.3 μm) | 0.4 (silver) |
|---|---|
| Gelatin | 0.6 |
| Sensitizing Dye I | $1.0 \times 10^{-4}$ |
| Sensitizing Dye II | $3.0 \times 10^{-4}$ |
| Sensitizing Dye III | $1 \times 10^{-5}$ |
| Coupler C-3 | 0.06 |
| Coupler C-4 | 0.06 |
| Coupler C-2 | 0.03 |
| Dispersing oil, Oil-1 | 0.03 |
| Dispersing oil, Oil-3 | 0.012 |

Fourth Layer: Second Red-Sensitive Emulsion Layer

| Silver iodobromide emulsion (silver iodide: 5 mol %, average particle diameter: 0.5 μm) | 0.7 |
|---|---|
| Sensitizing Dye I | $1 \times 10^{-4}$ |
| Sensitizing Dye II | $3 \times 10^{-4}$ |
| Sensitizing Dye III | $1 \times 10^{-5}$ |
| Coupler C-3 | 0.24 |
| Coupler C-4 | 0.24 |
| Coupler C-2 | 0.10 |
| Dispersing oil, Oil-1 | 0.15 |

-continued

| | |
|---|---|
| Dispersing oil, Oil-3 | 0.02 |

Fifth Layer: Third Red-Sensitive Emulsion Layer

| | |
|---|---|
| Silver iodobromide emulsion (silver iodide: 10 mol %, average particle diameter: 0.7 μm) | 1.0 (silver) |
| Gelatin | 1.0 |
| Sensitizing Dye I | $1 \times 10^{-4}$ |
| Sensitizing Dye II | $3 \times 10^{-4}$ |
| Sensitizing Dye III | $1 \times 10^{-5}$ |
| Coupler C-6 | 0.05 |
| Coupler C-7 | 0.1 |
| Coupler C-2 | 0.05 |
| Dispersing oil, Oil-1 | 0.01 |
| Dispersing oil, Oil-2 | 0.05 |

Sixth Layer: Intermediate Layer

| | |
|---|---|
| Gelatin | 1.0 |
| Compound Cpd-A | 0.03 |
| Dispersing oil, Oil-1 | 0.05 |

Seventh Layer: First Green-Sensitive Emulsion Layer

| | |
|---|---|
| Silver iodobromide emulsion (silver iodide: 4 mol %, average particle diameter: 0.3 μm) | 0.30 |
| Sensitizing Dye IV | $5 \times 10^{-4}$ |
| Sensitizing Dye VI | $0.3 \times 10^{-4}$ |
| Sensitizing Dye V | $2 \times 10^{-4}$ |
| Gelatin | 1.0 |
| Coupler C-9 | 0.2 |
| Coupler C-5 | 0.03 |
| Coupler C-1 | 0.03 |
| Dispersing oil, Oil-1 | 0.5 |

Eighth Layer: Second Green-Sensitive Emulsion Layer

| | |
|---|---|
| Silver iodobromide emulsion (silver iodide: 5 mol %, average particle diameter: 0.5 μm) | 0.4 |
| Sensitizing Dye IV | $5 \times 10^{-4}$ |
| Sensitizing Dye V | $2 \times 10^{-4}$ |
| Sensitizing Dye VI | $0.3 \times 10^{-4}$ |
| Coupler C-9 | 0.25 |
| Coupler C-1 | 0.03 |
| Coupler C-10 | 0.015 |
| Coupler C-5 | 0.01 |
| Dispersing oil, Oil-1 | 0.2 |

Ninth Layer: Third Green-Sensitive Emulsion Layer

| | |
|---|---|
| Silver iodobromide emulsion (silver iodide: 6 mol %, average particle diameter: 0.7 μm) | 0.85 (silver) |
| Gelatin | 1.0 |
| Sensitizing Dye VII | $3.5 \times 10^{-4}$ |
| Sensitizing Dye VIII | $1.4 \times 10^{-4}$ |
| Coupler C-11 | 0.01 |
| Coupler C-12 | 0.03 |
| Coupler C-13 | 0.20 |
| Coupler C-1 | 0.02 |
| Coupler C-15 | 0.02 |
| Dispersing oil, Oil-1 | 0.20 |
| Dispersing oil, Oil-2 | 0.05 |

Tenth Layer: Yellow Filter Layer

| | |
|---|---|
| Gelatin | 1.2 |
| Yellow colloidal silver | 0.08 |
| Compound Cpd-B | 0.1 |
| Dispersing oil, Oil-1 | 0.3 |

Eleventh Layer: First Blue-Sensitive Emulsion Layer

| | |
|---|---|
| Monodispersed silver iodobromide emulsion (silver iodide: 4 mol %, average particle diameter: 0.3 μm) | 0.4 (silver) |
| Gelatin | 1.0 |
| Sensitizing Dye IX | $2 \times 10^{-4}$ |
| Coupler C-14 | 0.9 |
| Coupler C-5 | 0.07 |
| Dispersing oil, Oil-1 | 0.2 |

Twelfth Layer: Second Blue-Sensitive Emulsion Layer

| | |
|---|---|
| Silver iodobromide emulsion (silver iodide: 10 mol %, average particle diameter: 1.5 μm) | 0.5 (silver) |
| Gelatin | 0.6 |
| Sensitizing Dye IX | $1 \times 10^{-4}$ |
| Coupler C-14 | 0.25 |
| Dispersing oil, Oil-1 | 0.07 |

Thirteenth Layer: First Protective Layer

| | |
|---|---|
| Gelatin | 0.8 |
| Ultraviolet Absorber UV-1 | 0.1 |
| Ultraviolet Absorber UV-2 | 0.2 |
| Dispersing oil, Oil-1 | 0.01 |
| Dispersing oil, Oil-2 | 0.01 |

Fourteenth Layer: Second Protective Layer

| | |
|---|---|
| Finely divided silver bromide (average particle diameters: 0.07 μm) | 0.5 |
| Gelatin | 0.45 |
| Particulate polymethyl methacrylate (diameter: 1.5 μm) | 0.2 |
| Hardener H-1 | 0.4 |
| Formaldehyde Scavenger S-1 | 0.5 |
| Formaldehyde Scavenger S-2 | 0.5 |

Besides the above compositions, a surface active agent is added to each layer as a coating assistant.

The chemical structure and chemical name of the compounds used in the example will be shown hereinafter.

UV-1

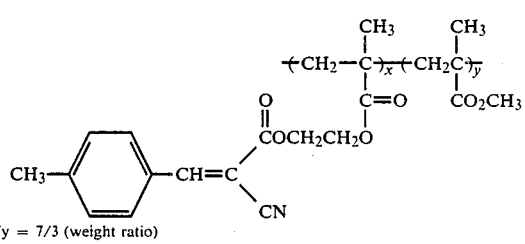

x/y = 7/3 (weight ratio)

UV-2

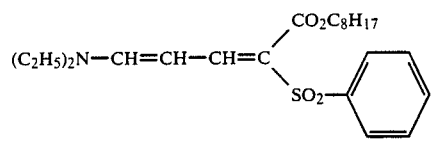
Oil-1: Tricresyl Phosphate
Oil-2: Dibutyl Phthalate
Oil-3: Bis(2-ethylhexyl) Phthalate
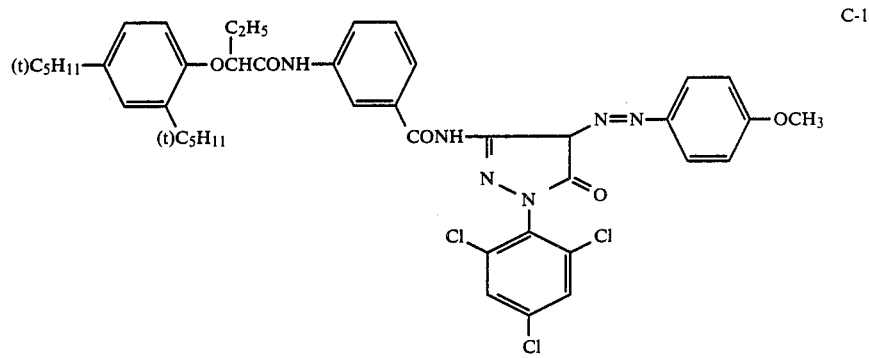
C-1
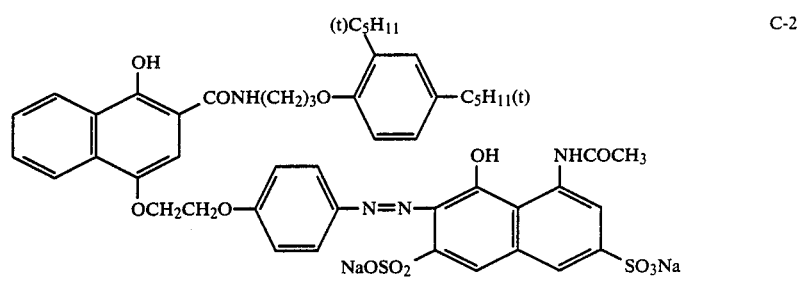
C-2
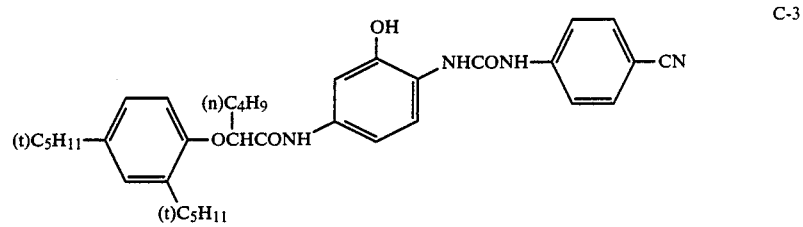
C-3
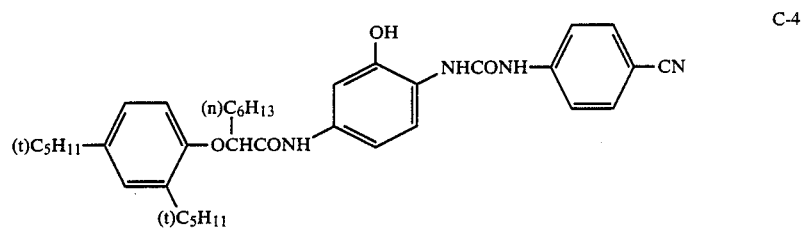
C-4
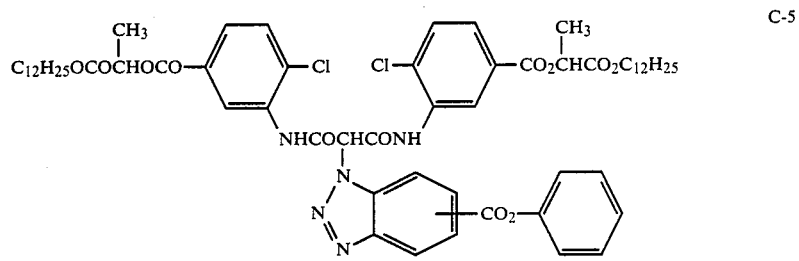
C-5

-continued
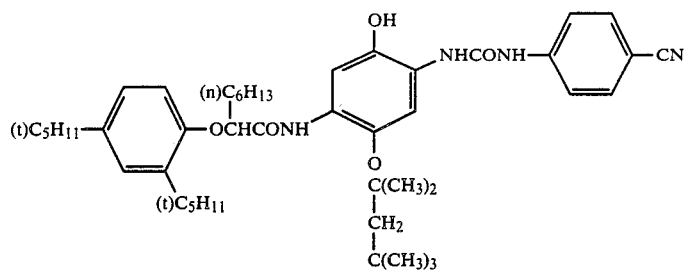
C-6
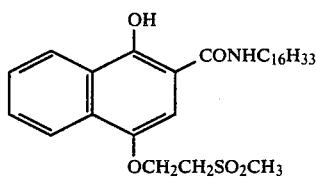
C-7
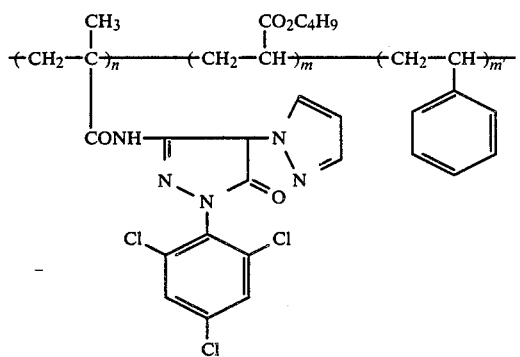
C-9
n/m/m' = 50/25/25 (wt %)
Average molecular weight: approx. 20,000
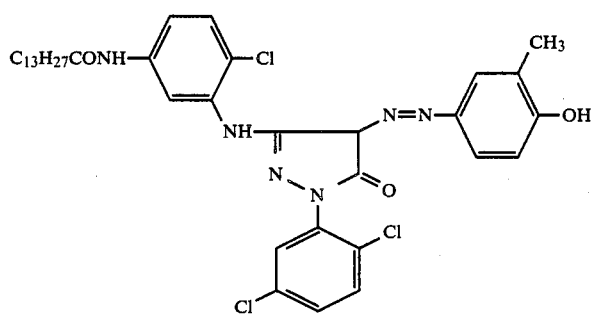
C-10
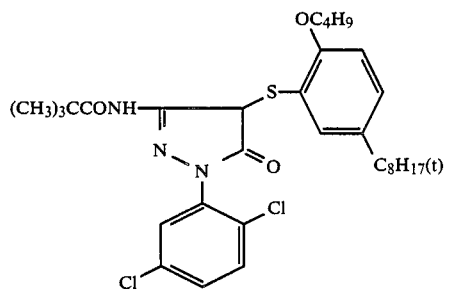
C-11

-continued
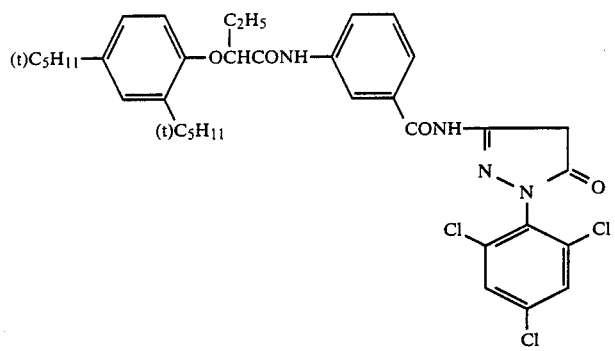
C-12
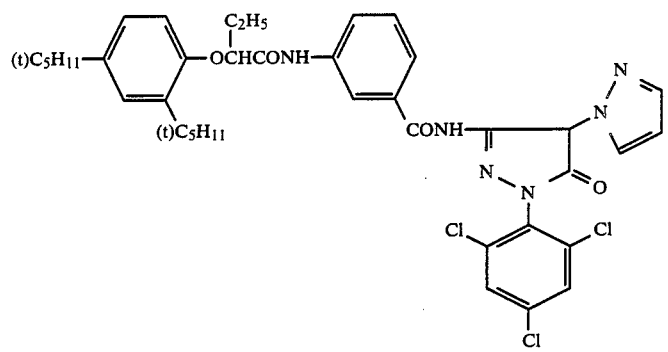
C-13
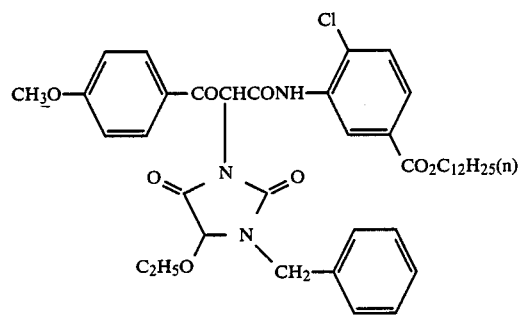
C-14
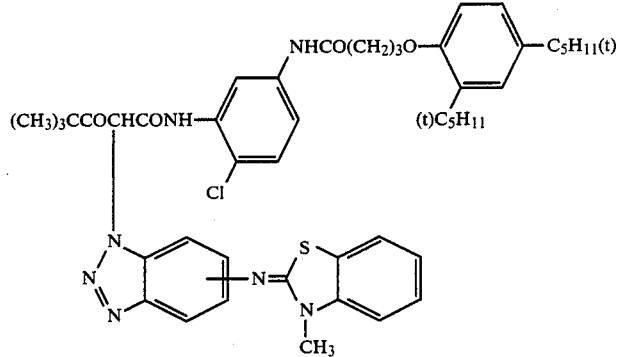
C-15
Cpd-A
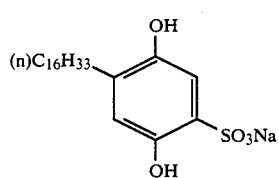
Cpd-B
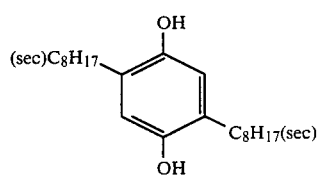

Sensitizing Dye I

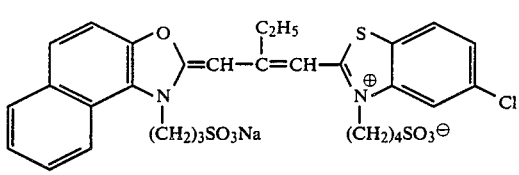

Sensitizing Dye II

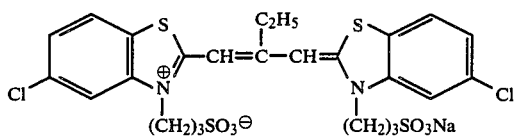

Sensitizing Dye III

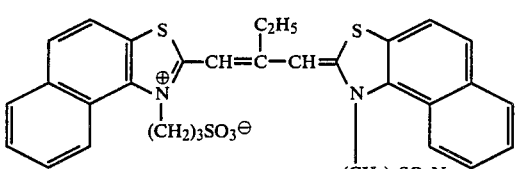

Sensitizing Dye IV

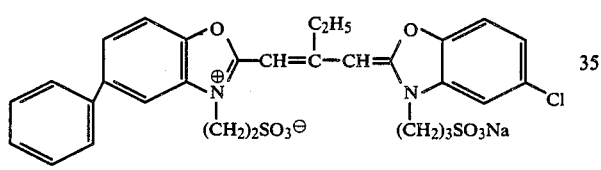

Sensitizing Dye V

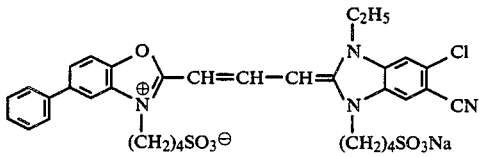

Sensitizing Dye VI

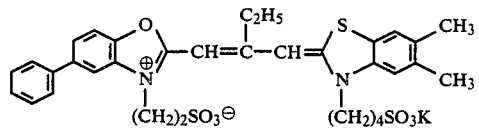

Sensitizing Dye VII

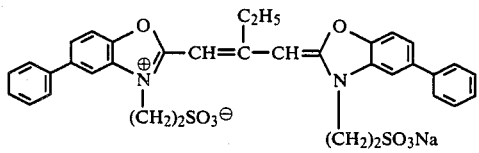

Sensitizing Dye VIII

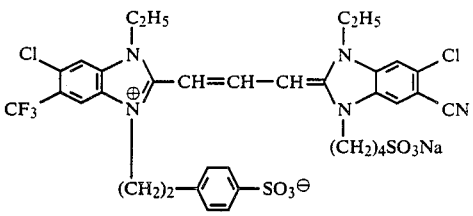

Sensitizing Dye IX

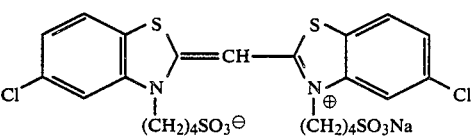

H-1

$CH_2=CHSO_2CH_2CONH-CH_2$
$CH_2=CHSO_2CH_2CONH-CH_2$

S-1

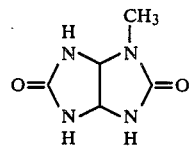

S-2

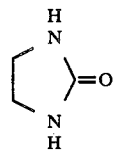

Specimen 301 thus prepared is cut to pieces of 35 m/m in width. These pieces are then used to photograph a standard object outdoors. These specimens are then subjected to the following process by means of an automatic developing machine.

TABLE 3

| | Processing Steps (temperature: 38° C.) | | |
|---|---|---|---|
| Step | Processing Time | Tank Volume (l) | Amount of Supply* (ml) |
| Color Development | 3 min 15 sec | 18 | 19 |
| Bleaching | 2 min 00 sec | 18 | 18 |
| Rinsing | 2 min 00 sec | 18 | 1,200 |
| Fixing | 3 min 15 sec | 18 | 33 |
| Rinsing (1) | 1 min 30 sec | 9 | — |
| Rinsing (2) | 1 min 30 sec | 9 | 25 |
| Stabilizing | 1 min 05 sec | 9 | 33 |

*Value per 1 m of light-sensitive material of 35 m/m width.

In the above processing steps, Rinsings (1) and (2) are conducted in a countercurrent system in which rinse water flows from the bath for Rinsing (2) to that for Rinsing (1). The composition of each processing solution will be described hereinafter.

Color Developing Solution

The compositions of the mother solution and the replenisher of the color developing solution are as follows:

|  | Mother Solution | Replenisher |
|---|---|---|
| Diethylenetriaminepentaacetic Acid | 0.8 g | 0.8 g |
| 1-Hydroxyethylidene-1,1-diphosphonic Acid | 3.3 g | 3.3 g |
| Sodium Sulfite | 4.0 g | 4.5 g |
| Potassium Carbonate | 30.0 g | 39.0 g |
| Potassium Bromide | 1.4 g | 0.3 g |
| Potassium Iodide | 1.3 mg | 0 |
| Hydroxylamine Sulfate | 2.4 g | 3.0 g |
| 4-(N—Ethyl-N—β-hydroxyethyl-amino)-2-methylaniline Sulfate | 4.5 g | 6.4 g |
| Water to make | 1.0 l | 1.0 l |
| pH | 10.0 | 10.15 |

The pH adjustment is effected by using potassium hydroxide or sulfuric acid.

Bleaching Solution

|  | Mother Solution | Replenisher |
|---|---|---|
| Ammonium Ethylenediamine-tetraacetato Ferrate | 100 g | 110 g |
| Disodium Ethylenediamine-tetraacetate | 10 g | 11 g |
| Ammonia Water | 3 ml | 2 ml |
| Ammonium Nitrate | 10.0 g | 12.0 g |
| Ammonium Bromide | 150 g | 170 g |
| Water to make | 1 l | 1 l |
| pH | 6.0 | 5.8 |

Fixing Solution

|  | Mother Solution | Replenisher |
|---|---|---|
| Disodium Ethylenediamine-tetraacetate | 1.0 g | 1.2 g |
| Sodium Sulfite | 4.0 g | 5.0 g |
| Sodium Bisulfite | 4.6 g | 5.8 g |
| Aqueous Solution of Ammonium Thiosulfate (70%) | 175 ml | 200 ml |
| Water to make | 1 l | 1 l |
| pH | 6.6 | 6.6 |

Stabilizing Solution

|  | Mother Solution | Replenisher |
|---|---|---|
| Formalin (37% w/v) | 2.0 ml | 3.0 ml |
| Polyoxyethylene-p-monononyl-phenyl Ether (average polymerization degree: 10) | 0.3 g | 0.45 g |
| Water to make | 1 l | 1 l |

Specimen 301 (35 m/m width) which was used to photograph the standard object outdoors was processed for 50 m a day for three consecutive days by means of an automatic developing machine having the tank volume described in Table 3. The concentration of Fe(II) in the bleach bath thus used for the 3-day processing was measured by the above mentioned method. The result was $2 \times 10^{-3}$ mol/l.

Specimens prepared by using this processing solution in the following manner are subjected to exposure to light and processed in the same manner as in Example 1.

Specimens 302 to 304 are prepared in the same manner as in Specimen 301 except that Coupler C-2 is replaced by the equimolecular coupler should in Table 4. However, for the present specimens, equimolecular weight of Coupler C-7 are added to make gradation thereof substantially level with each other.

The results are shown in Table 4.

TABLE 4

| Specimen No. | Added Amount of Masking Coupler | Sensitivity | Masking |
|---|---|---|---|
| 301 (Comparison) | C-2 (control) | −0.10 | 0.12 |
| 302 (Comparison) | B-1 (3 time mol) | ±0 (control) | 0.03 |
| 303 (Invention) | (1) (3 time mol) | +0.01 | 0.10 |
| 304 (Invention) | (3) (3 time mol) | +0.02 | 0.09 |
| 305 (Invention) | (9) (3 time mol) | +0.02 | 0.08 |

Table 4 shows that the present specimens cause no reduction in sensitivity and have a great masking effect.

EXAMPLE 4

A specimen is prepared in the same manner as in Example 1 except that the couplers are replaced by 1.5 g/m² of the present Compound (17).

The specimen thus prepared is exposed to light in the same manner as in Example 1 and then subjected to the following black-and-white development.

As a result, a reversal image is obtained imagewise. The color image is stable to light and heat.

Processing Step (processing temperature: 20° C.)

| Developing Solution | 7 min |
|---|---|
| Bleaching Solution | 10 min |
| Rinsing | 10 min |
| Iron (II) Bath | 10 min |
| Fixing Bath | 5 min |
| Rinsing | 10 min |

Preparation of Processing Solution
Developing Solution:

| Phenidone | 2 g |
|---|---|
| Sodium Sulfite | 50 g |
| Hydroquinone | 5 g |
| Borax.5H₂O | 1.53 g |
| Water to make | 1 l |

The other processing solutions are the same as used in Example 1.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having provided thereon at least one layer containing a compound represented by the general formula (II):

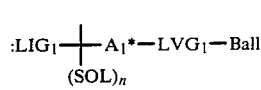

(II)

wherein LIG₁ represents a group which reacts with metal ions at the ":" side to form a complex compound so that it colors; A₁* represents a coupling group or an oxidation reduction group; when A₁* is a coupling group, * represents a coupling position whereas when A₁* represents an oxidation reduction group, the position at which A₁* undergoes a nucleophilic addition by a nucleophilic species present during development upon crossoxidation is represented by *; LVG$_1$ represents a coupling-off group which is linked to * of A$_1$; Ball represents an organic group for making the molecule of the compound large enough to be rendered diffusion resistant; SOL represents a dissociating group or a quaternary ammonium salt for rendering the molecule of the compound water-soluble after a A$_1$*—LVG$_1$ bond cleavage so that it effuses from the light-sensitive material; SOL links to any position of :LIG$_1$—A$_1$*—; and n represents an integer of 0 to 3, with the proviso that Ball may contain a $$:LIG_1\!-\!\!\!\underset{(SOL)_n}{\!\!|\!\!}\!\!-\!A_1^*\!-\!LVG_1\!-$$

group wherein the compound of the general formula (II) is a bis compound or a polymer compound.

2. A silver halide color photographic material of claim 1 further comprising a color image forming coupler, wherein the molar ratio of the compound of formula II to the color image forming coupler is 0.1/99.9 to 90/10.

3. A silver halide color photographic material of claim 1, wherein A$_1$* is represented by the general formulae (Cp-1), (Cp-2), (Cp-3), (Cp-4), (Cp-5), (Cp-6), (Cp-7), (Cp-8), (Cp-9) and (Cp-10):

(Cp-1)
$$R_{51}-\overset{O}{\underset{\|}{C}}-\underset{\underset{*}{|}}{CH}-\overset{O}{\underset{\|}{C}}-NH-R_{52}$$

(Cp-2)
$$R_{53}-NH-\overset{O}{\underset{\|}{C}}-\underset{\underset{*}{|}}{CH}-\overset{O}{\underset{\|}{C}}-NH-R_{52}$$

(Cp-3)

(Cp-4)

(Cp-5)

(Cp-6)

(Cp-7)

(Cp-8)

(Cp-9)

(Cp-10)

wherein the free bond —* which comes from the coupling position represents the position at which the coupling-off group (—LVG$_1$—Ball) is connected thereto; R$_{51}$, R$_{52}$, R$_{53}$, R$_{54}$, R$_{55}$, R$_{56}$ and R$_{57}$ each represents a hydrogen atom or another substituent; a coupling group is connected to :LIG$_1$— and SOL at these positions directly or through these substituents as divalent groups; if the coupling group does not contain a group represented by :LIG$_1$ or SOL, then R$_{51}$, R$_{52}$, R$_{53}$, R$_{54}$, R$_{55}$, R$_{56}$ and R$_{57}$ are properly selected from known substituents for the purpose of controlling the rate of coupling; and q represents an integer of 1 to 3, p represents an integer of 1 to 5, and l represents an integer of 1 to 4.

4. A siler halide color photographic material of claim 1, wherein A* is represented by the general formula (R-1):

$$B_1-P-(X=Y)_m-Q-B_2 \qquad (R\text{-}1)$$

wherein P and Q each represents an oxygen atom or a substituted or unsubstituted imino group, P and Q being different from each other; m represents an integer of 1 to 3; at least one of X and Y represents a methine group containing —LVG$_1$—Ball as a substituent and at least one of the remaining X and Y represents a methine group containing :LIG$_1$— as a substituent; when SOL is contained in the molecule of the compound, SOL may be contained in the substituent containing LIG$_1$— or at least one of the remaining X and Y represents a methine group containing SOL; B$_1$ and B$_2$ each represents a group which can be removed by a hydrogen atom or alkali; and any two substituents of P, X, Y, Q, B$_1$ and B$_2$ may be connected to each other as divalent groups to form a cyclic structure.

5. A silver halide color photographic material of claim 4, wherein P and Q each is represented by the general formulae (R-2) and (R-3):

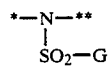  (R-2)

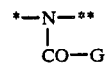  (R-3)

wherein * represents the position at which P or Q is connected to $B_1$ or $B_2$; and ** represents the position at which P or Q is connected to one of the free bonds of $-(X=Y)_m-$; the group represented by G is a $C_{1-32}$ straight chain, branched or cyclic, saturated or unsaturated, substituted or unsubstituted aliphatic gorup, a $C_{6-10}$ substituted or unsubstituted aromatic group, or a 4-membered to 7-membered heterocyclic group comprising nitrogen atoms, sulfur atoms or oxygen atoms as hetero atoms.

6. A silver halide color photographic material of claim 4, wherein $B_1$ and $B_2$ each represents a precursor group which can be removed by an alkali, and wherein the precursor group is selected from the group consisting of hydrolyzable groups, precursor groups of the type utilizing reverse Michael reaction, precursor groups of the type utilizing as an intramolecular nucleophilic group an anion produced after ring cleavage reaction, precursor groups which cause a cleavage reaction by an electron transfer of anions through a conjugated system, precursor groups which cause a cleavage reaction by an electronic transfer of anions which have undergone a reaction after a ring cleavage, and precursor groups utilizing an imidemethyl group.

7. A silver halide color photographic material of claim 4, wherein P represents an oxygen atom and $B_2$ represents a hydrogen atom.

8. A silver halide color photographic material of claim 4, wherein (X=Y— forms a benzene ring.

9. A silver halide color photographic material of claim 4, wherein said compound represented by general formula (R-1) is represented by the general formula (R-4) or (R-5):

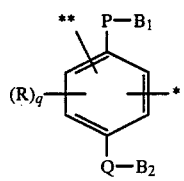  (R-4)

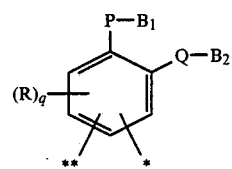  (R-5)

wherein * represents the position at which $LVG_1$-Ball is connected thereto; ** represents the position at which a substituent containing: $LIG_1$- is connected thereto; wherein P and Q each represents an oxygen atom or a substituted or unsubstituted imino group, P and Q being different from each other; $B_1$ and $B_2$ each represents a group which can be removed by a hydrogen atom or alkali; any two substituents of P, Q, $B_1$ and $B_2$ may be connected to each other as divalent groups to form a cyclic structure; R represents a substituent; q represents an integer of 0 to 2; when q is 2 or more, R may be the same or different; and when two R groups are substituents connected to adjacent carbon atoms, they may be connected to each other as divalent groups to represent a cyclic structure.

10. A silver halide color photographic material of claim 1, wherein $LVG_1$ is a compound represented by any one of the general formulae (L-1), (L-2) and (L-3):

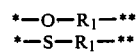  (L-1)
  (L-2)

  (L-3)

wherein * represents the position at which the compound is connected to $A_1$*; ** represents the position at which the compound is connected to Ball; $R_1$ represents a divalent aromatic group, a divalent aliphatic group or a divalent heterocyclic group; $R_2$ represents an organic residual group for forming a nitrogen-containing heterocyclic group; and $R_1$ and $R_2$ may contain substituents besides Ball at any possible position.

11. A silver halide color photographic material of claim 1, wherein the group represented by: $LIG_1$ contains the following partial structures:

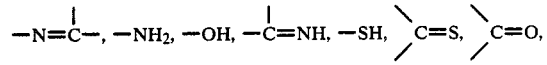

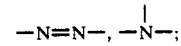

and the hetero atoms in these groups or anions of these dissociated forms are in such a steric position that they form a chelate with metal ions involving the formation of a 4- to 7-membered ring.

12. A method of processing said silver halide color photographic material of claim 1, which comprises:
 (i) image-wise exposing said color photographic material to light,
 (ii) developing said color photographic material, and
 (iii) processing said color photographic material through a processing solution containing an iron (II) ion concentration of $1 \times 10^{-6}$ to 1 mol/l.

13. A method of claim 12, wherein said iron (II) ion concentration is $1 \times 10^{-4}$ to 1 mol/l.

14. A method of claim 12, wherein said iron (II) ion concentration is $1 \times 10^{-3}$ to 1 mol/l.

15. A method of processing said silver halide color photographic material of claim 1, which comprises:
 (i) image-wise exposing said color photographic material to light,
 (ii) developing said color photographic material, and
 (iii) processing said color photographic material through a bath having bleaching capacity and which contains an aminopolycarboxylic acid-iron (III) complex salt, wherein the potential of the bath is 150 mV or less.

16. A method of claim 15, wherein said potential is 120 mV or less.

17. A method of claim 15, wherein said potential is 100 mV or less.

18. A silver halide color photographic material of claim 1, wherein: $LIG_1$ is selected from the group consisting of terpyridine, bipyridine, hydrazone, tetrazolylpyridine, pyridylquinazoline, imine, bisisoquinoline, phenanthroline, bidiazine, pyridyldiazine, pyridylbenzimidazole, phenol, biimidazole, diazyltriazine, o-nitrosoaniline, tetrazine, triazine, oxime, imidazolylpyridine, polypyrrole and hydroxyanthraquinone.

19. A silver halide color photographic material of claim 1, wherein the amount of the compound of formula II is $1 \times 10^{-7}$ to 1.0 mol per mol of silver.

* * * * *